United States Patent [19]

Chen

[11] Patent Number: 6,050,871
[45] Date of Patent: Apr. 18, 2000

[54] CRYSTAL GEL AIRFOILS WITH IMPROVED TEAR RESISTANCE AND GEL AIRFOILS WITH PROFILES CAPABLE OF EXHIBITING TIME DELAY RECOVERY FROM DEFORMATION

[75] Inventor: John Y. Chen, Pacifica, Calif.

[73] Assignee: Applied Elastomerics, Inc., South San Francisco, Calif.

[21] Appl. No.: 08/909,487

[22] Filed: Aug. 12, 1997

Related U.S. Application Data

[63] Continuation-in-part of application No. 08/581,125, Dec. 29, 1995, Pat. No. 5,962,572, application No. 08/581,188, Dec. 29, 1995, abandoned, application No. 08/581,191, Dec. 29, 1995, Pat. No. 5,760,117, application No. 08/845,809, Apr. 29, 1997, Pat. No. 5,938,499, application No. 08/863,794, May 27, 1997, application No. 08/819,675, Mar. 17, 1997, Pat. No. 5,884,639, application No. 08/719,817, Sep. 30, 1996, application No. 08/665,343, Jun. 17, 1996, application No. 08/612,586, Mar. 8, 1996, application No. PCT/US94/07314, Jun. 27, 1994, application No. PCT/US94/04278, Apr. 19, 1994, and application No. 08/288,690, Aug. 11, 1994, Pat. No. 5,633,286.

[51] Int. Cl.$^7$ ..................................................... A63H 27/00

[52] U.S. Cl. .................. 446/46; 446/48; 446/486
[58] Field of Search ................................. 446/486, 46, 48

[56] References Cited

U.S. PATENT DOCUMENTS

| | | | |
|---|---|---|---|
| 4,737,128 | 4/1988 | Moormann et al. | 446/46 |
| 5,026,054 | 6/1991 | Osher et al. | 446/46 |
| 5,324,222 | 6/1994 | Chen | 446/46 |
| 5,655,947 | 8/1997 | Chen | 446/46 |
| 5,868,597 | 2/1999 | Chen | 446/46 |

FOREIGN PATENT DOCUMENTS 1268431  3/1972  United Kingdom .

*Primary Examiner*—Herbert J. Lilling

[57] ABSTRACT

A novel aerodynamic toy comprising a camber defined by one or more inner or outer parameter gel profile(s) in the shape of an airfoil made from an elastic, tear resistant, crystal gel with or without one or more outer parameter gel profile(s) having a connective thin gel membrane, said gel membrane having one or more preselected holes therethrough. The airfoils of the invention exhibits excellent flight stability and no turnover.

8 Claims, 10 Drawing Sheets

CRYSTAL GEL AIRFOILS WITH IMPROVED TEAR RESISTANCE AND GEL AIRFOILS WITH PROFILES CAPABLE OF EXHIBITING TIME DELAY RECOVERY FROM DEFORMATION

RELATED APPLICATIONS AND PATENTS

This application is a continuation-in-part application of applications U.S. Ser. No. 08/581,125 filed Dec. 29, 1995 (now U.S. Pat. No. 5,962,572); Ser. No. 08/581,188 filed Dec. 29, 1995 (now abandoned); Ser. No. 08/581,191 Dec. 29, 1995 (now U.S. Pat. No. 5,760,117); Ser. No. 08/845,809 filed Apr. 29, 1997 (now U.S. Pat. No. 5,938,499); Ser. No. 08/863,794 filed May 27, 1997; Ser. No. 08/819,675 filed Mar. 17, 1997 (now U.S. Pat. No. 5,884,639); Ser. No. 08/719,817 filed Sep. 30, 1996; Ser. No. 08/665,343 filed Jun. 17, 1996; U.S. Pat. No. 612,586 filed Mar. 8, 1996; PCT/US/94/07314 Filed Jun. 27, 1994 (now U.S. Pat. No. 5,868,597), PCT/US94/04278, filed Apr. 19, 1994 (now U.S. Ser. No. 08/211,781); Ser. No. 288,690 filed Aug. 11, 1994 (now U.S. Pat. No. 5,633,286). The subject matter contained in the related applications and patents are specifically incorporated herein by reference.

FIELD OF THE INVENTION

The present invention relates to novel compositions and aerodynamic toys.

BACKGROUND OF THE INVENTION

The closest known art are: UK patent 1,268,431 discloses a symmetric gel ball. U.S. Pat. No. 5,026,054 discloses a highly plasticized polymeric symmetric shaped annular core encased in a flexible polymer shell and further encased in a stretchable fabric outer cover. U.S. Pat. Nos. 4,369,284 and 4,618,213 discloses gel compositions and gel articles including gel optical lens. U.S. Pat. No. 4,737,128 discloses a (concave top shape and convex bottom shape) airfoil resilient enough so that when resting on a horizontal surface, its outer annular edge will be able to support the entire airfoil without the airfoil's interior portion touching the horizontal surface on which it rests. A gel ring for looping over the thumb and pulled back on the other end can be shot like a rubber band and routinely achieve shots of 25 to 30 feet is available from Applied Elastomerics, Inc., of South San Francisco, Calif. under the tradename "SMARTRING".

SUMMARY OF THE INVENTION

I have unexpectedly discovered improved aerodynamic toys comprising a camber defined by a profile in the shape of an airfoil made from improved high tear resistance crystal gel compositions and crystal gel compositions having novel time delay recovery properties; optionally, said airfoil having one or more inner or outer parameter gel profile(s); said one or more outer parameter gel profile(s) having a connective thin gel membrane, said gel membrane with or without one or more preselected holes therethrough. The compositions of the gel airfoils of the invention comprises: (I) 100 parts by weight of one or more high viscosity linear, branched, star-shaped (radial), or multiarm block copolymers or mixtures of two or more such block copolymers, said block copolymers having one or more midblocks, said midblocks comprising one or more substantially crystalline polyethylene midblocks and with nil, one or more amorphous midblocks; optionally in combination with a selected amount of one or more of a (II) polymer or copolymer, and selected amounts of a plasticizing oil (III) sufficient to achieve gel rigidities of from less than about 2 gram Bloom to about 1,800 gram Bloom with the proviso that said block copolymers having nil amorphous midblocks are combined with at least one block copolymer having at least one amorphous midblock.

As used herein, the term "gel rigidity" in gram Bloom is determined by the gram weight required to depress a gel a distance of 4 mm with a piston having a cross-sectional area of 1 square centimeter at 23° C.

The gels comprising thermoplastic elastomer block copolymers having one or more substantially crystalline polyethylene midblocks of the invention are hereafter referred to as "elastic-crystalline gels" or simpler "crystal gels". The block midblocks of copolymers forming the crystal gels of the invention are characterized by sufficient crystallinity as to exhibit a melting endotherm of at least about 40° C. as determined by DSC curve.

The various types of high viscosity block copolymers employed in forming the crystal gels of the invention are of the general configurations A-Z-A and $(R-Z)_n$, wherein the subscript n is two or more. In the case of multiarm block copolymers where n is 2, the block copolymer denoted by $(A-Z)_n$ is A-Z-A. It is understood that the coupling agent is ignored for sake of simplicity in the description of the $(A-Z)_n$ block copolymers.

The end block segment (A) comprises a glassy amorphous polymer end block segment, preferably, polystyrene. The midblocks (Z) comprises one or more midblocks of substantially crystalline poly(ethylene) (simply denoted by "-E- or (E)") with or without one or more amorphous midblocks of poly(butylene), poly(ethylene-butylene), poly(ethylene-propylene) or combination thereof (the amorphous midblocks are denoted by "-B- or (B)", "-EB- or (EB)", and "-EP- or (EP)" respectively or simply denoted by "-W- or (W)" when referring to one or more of the amorphous midblocks as a group) The A and Z portions are incompatible and form a two or more-phase system consisting of sub-micron amorphous glassy domains (A) interconnected by (Z) chains. The glassy domains serve to crosslink and reinforce the structure. This physical elastomeric network structure is reversible, and heating the polymer above the softening point of the glassy domains temporarily disrupt the structure, which can be restored by lowering the temperature.

The (I) linear block copolymers are characterized as having a Brookfield Viscosity value at 5 weight percent solids solution in toluene at 30° C. of from less than about 40 cps to about 60 cps and higher, advantageously from about 40 cps to about 160 cps and higher, more advantageously from about 50 cps to about 180 cps and higher, still more advantageously from about 70 cps to about 210 cps and higher, and even more advantageously from about 90 cps to about 380 cps and higher.

The (I) branched, star-shaped (radial), or multiarm block copolymers are characterized as having a Brookfield Viscosity value at 5 weight percent solids solution in toluene at 30° C. of from about 80 cps to about 380 cps and higher, advantageously from about 150 cps to about 260 cps and higher, more advantageously from about 200 cps to about 580 cps and higher, and still more advantageously from about 100 cps to about 800 cps and higher.

The crystal gels can be made in combination with a selected amount of one or more selected polymers and copolymers (II) including thermoplastic crystalline polyurethane elastomers with hydrocarbon blocks, homopolymers, copolymers, block copolymers, polyethylene copolymers, polypropylene copolymers, and the like described below.

The crystal gels forming the airfoils of the invention are also suitable in physically interlocking or forming with other selected materials to form airfoil composites combinations. The materials are selected from the group consisting of foam, plastic, fabric, various natural and synthetic fibers and films.

The various aspects and advantages of the invention will become apparent to those skilled in the art upon consideration of the accompanying disclosure and the drawings.

DESCRIPTION OF THE PREFERRED EMBODIMENTS

Figure 1A:
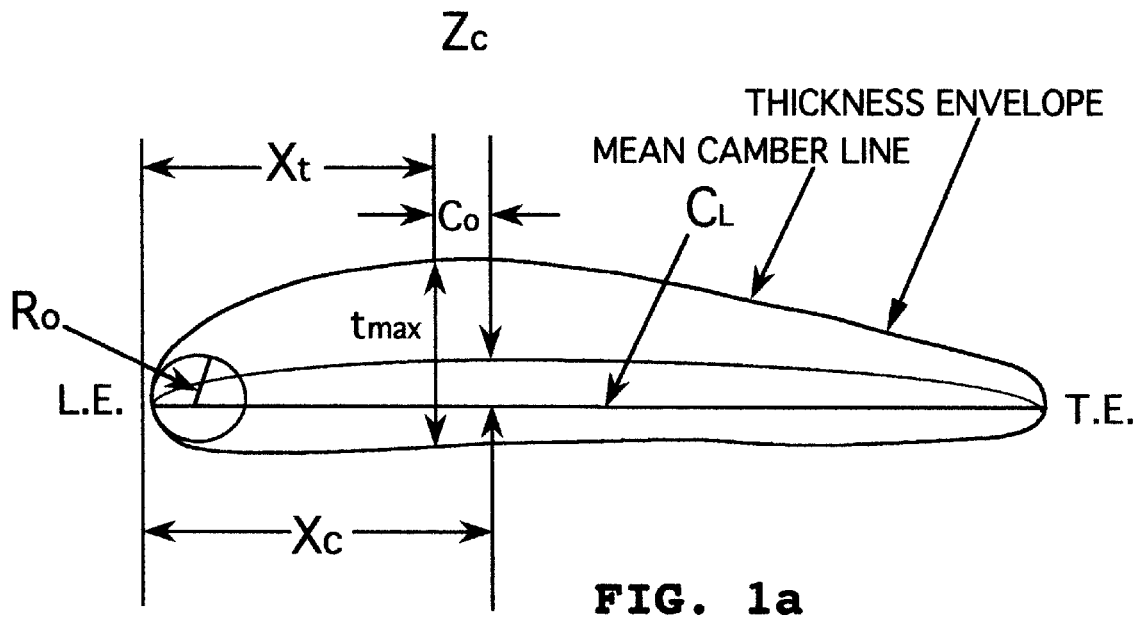
FIG. 1a. Representative static view of a spinning airfoil (at an elongation of at least 200%) showing various geometrical variables.

The shapes and profiles of the airfoils which can be made from the novel tear resistant and time delay recovery crystal gel compositions of the present invention are shown in the above representative drawings and described in my U.S. Pat. No. 5,324,222 and copending U.S. application Ser. No. 07/705,096 now U.S. Pat. No. 5,655,947 and Ser. No. 08/256,235 filed as PCT/US 94/07314. The conventional amorphous (non-crystalline) SEBS based gels such as described in my U.S. Pat. Nos.: U.S. Pat. Nos. 4,369,284; 4,618,213; 5,153,254; 5,239,723; 5,262,468; 5,324,222; 5,334,646; 5,336,708; 5,475,890; 5,508,334; 5,624,290; 5,633,286; and 5,655,947 are easy to tear. Tearing of the SEBS gel airfoils has been of major concern from the beginning. The subject matter contained in these patents and publications are specifically incorporated herein by reference.

In general, amorphous gels such as those made form SEBS and SEPS can fail catastrophically when subjected repeatedly to applied forces of high dynamic and static deformations, such as extreme compression, torsion, high tension, high elongation, and the like. Additionally, the development of cracks or crazes resulting from a large number of deformation cycles can induce catastrophic fatigue failure of amorphous gel composites, such as tears and rips between the surfaces of the amorphous gel and substrates or at the interfaces of interlocking material(s) and gel. Consequently, such amorphous gels are inadequate for the most demanding applications involving endurance at high stress and strain levels over an extended period of time. Consequently, when the airfoil is cut or notched during use, the resulting catastrophic failure renders the toy useless.

As described below, the high tear resistance compositions and unique compositions having novel time delay recovery properties are of great advantage for use in making the crystal gel airfoils of the present invention.

The crystal gel airfoils of the present invention are not limited to any particular aerodynamic inner or outer parameter gel profiles, although certain gel profiles may have advantages over others such as for speed, distance, climb, stall, return, etc. The basic principles of aerodynamics and airfoil design can be utilized to assist in selecting and forming the gel profiles of the airfoils of the invention. In designing the airfoils of the invention, Bernoulli's principle should be kept in mind, in simple words: in a nonviscous flow a deceleration is accompanied by a rise in pressure along the streamline; conversely, in an acceleration, there must be a fall in pressure along the streamline. More simply, the conditions are: along a particular streamline: (1) where the air speed is high, the air pressure is low; and (2) where the air speed is low, the air pressure is high.

Generally, any aerodynamic inner or outer parameter gel profiles can be selected for use in the design of the crystal gel airfoil of the invention provided the profile selected gives the airfoil (when launched by hand) a sustained flight-time in air that is greater than the time required for the airfoil to fall the vertical distance to the ground in free-fall when released from the same launch height.

Figure 1B:
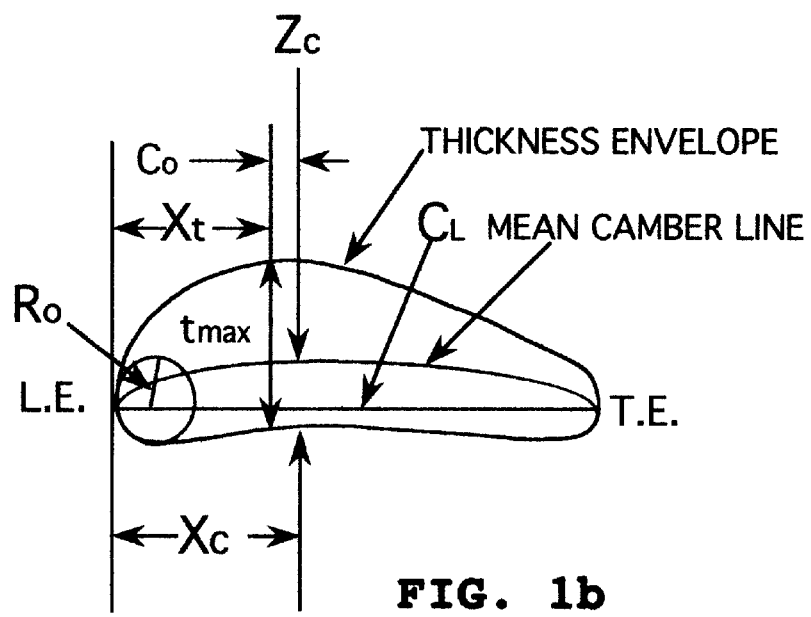
FIG. 1b. Representative normal view of the airfoil of FIG. 1a (at zero elongation) showing various geometrical variables.
Figure 2:
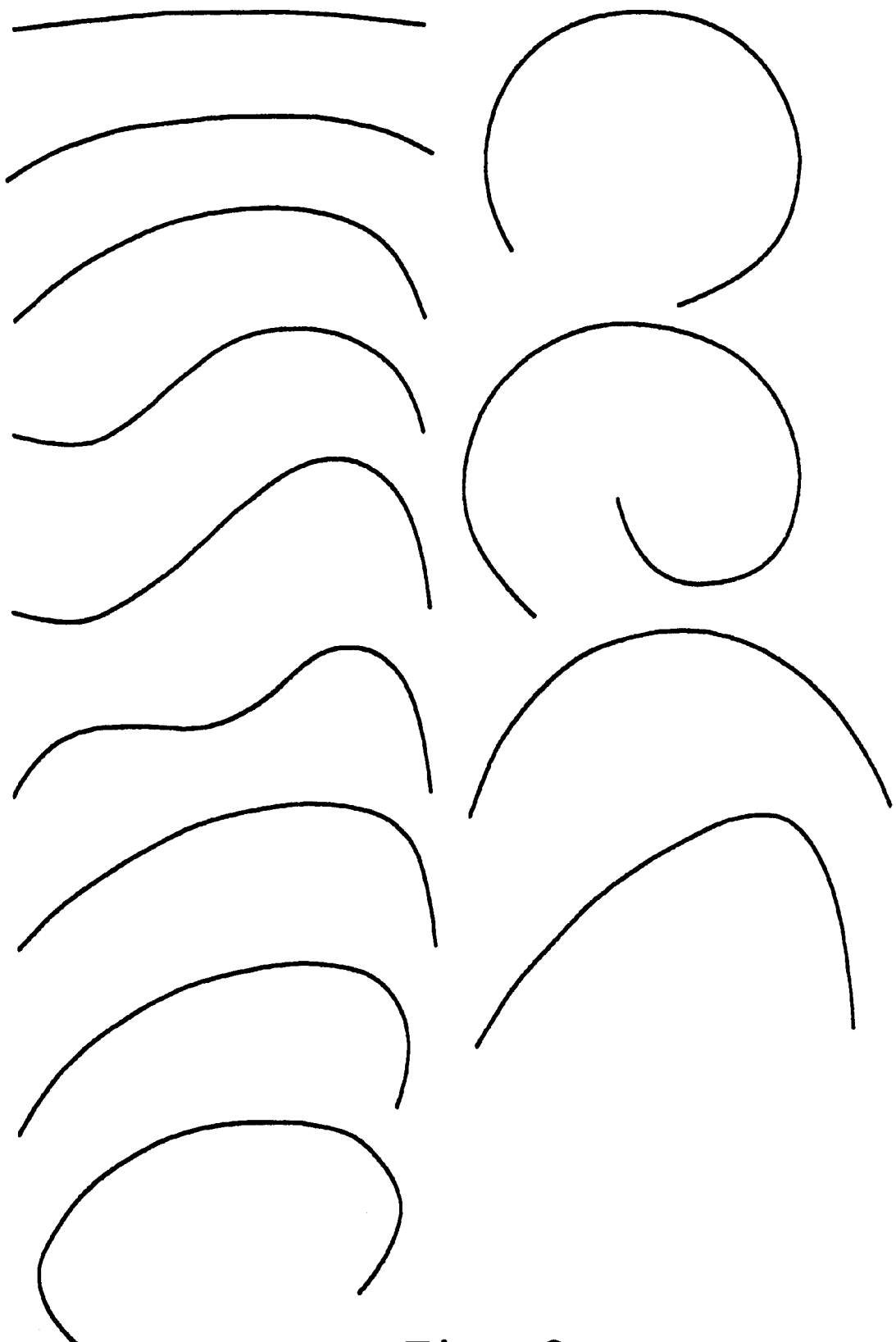
FIG. 2. Line view of selected examples of mean camber lines of airfoils of the invention.
Figure 3:
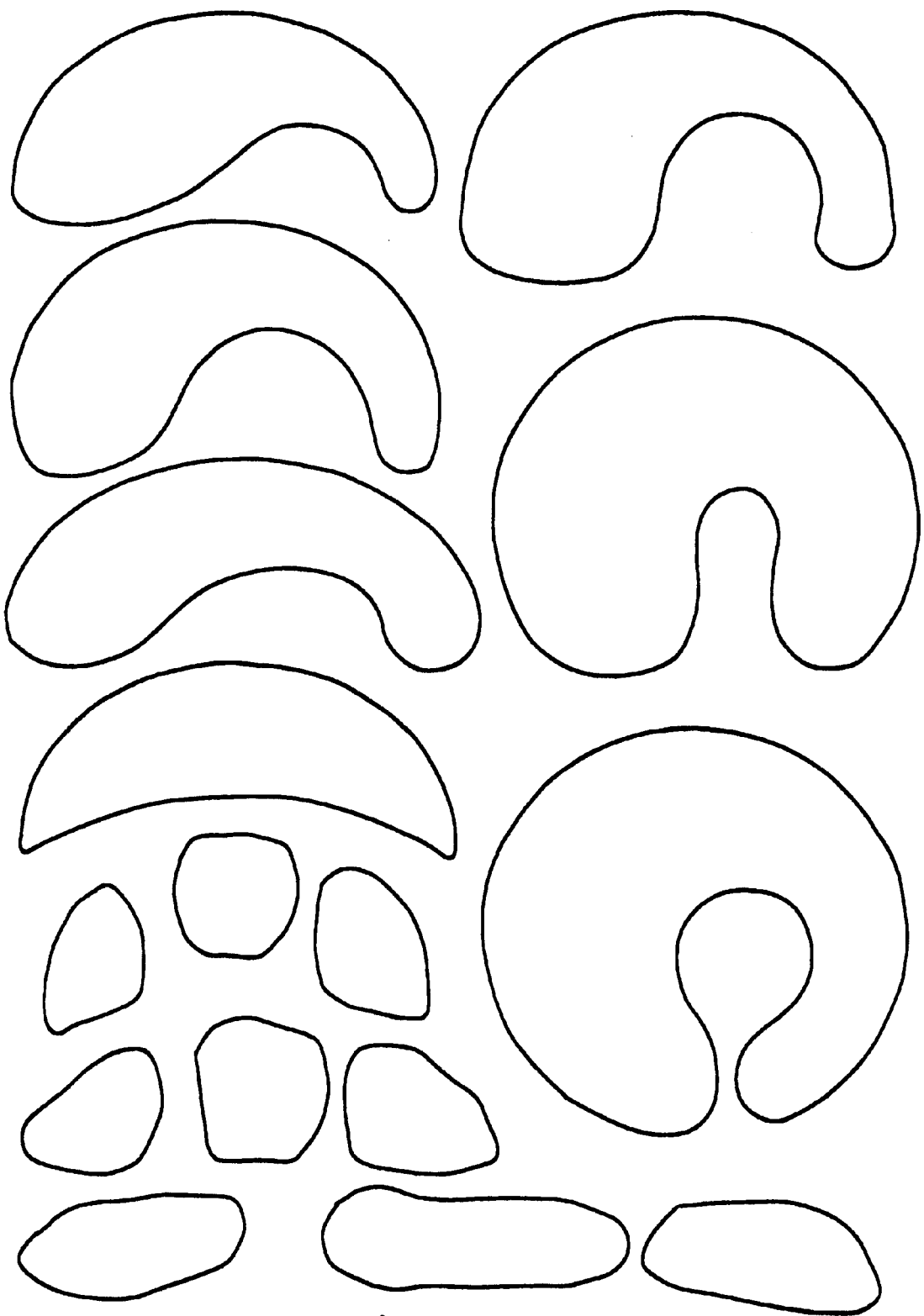
FIG. 3. Side view of various representative profile cross section imprint tracings of airfoils of the invention including an imprint of one of the airfoils at an elongation greater than 200%.
Figure 4:
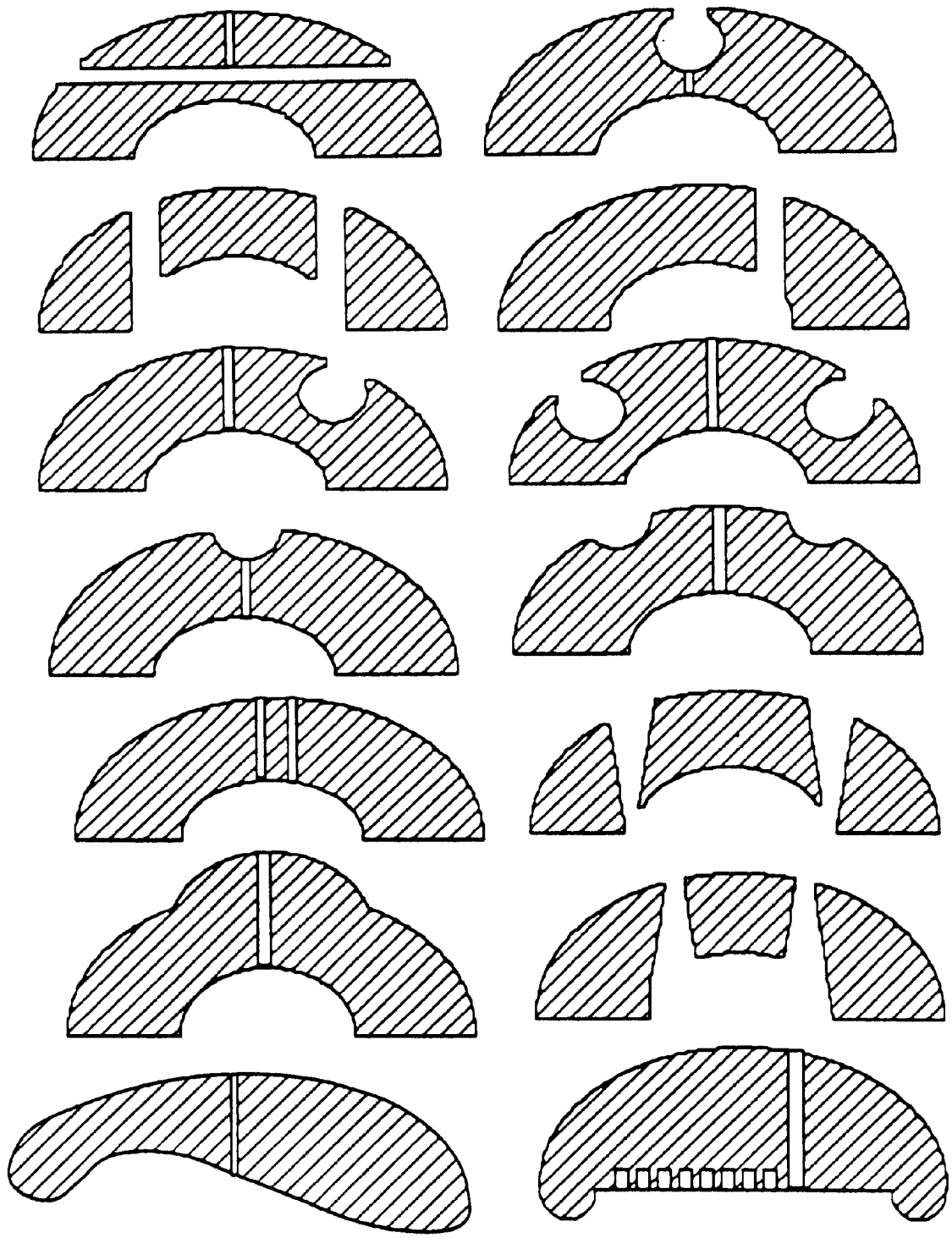
FIG. 4. Representative sectional views of shaped airfoils with holes, cavities, and slots.
Figure 5:
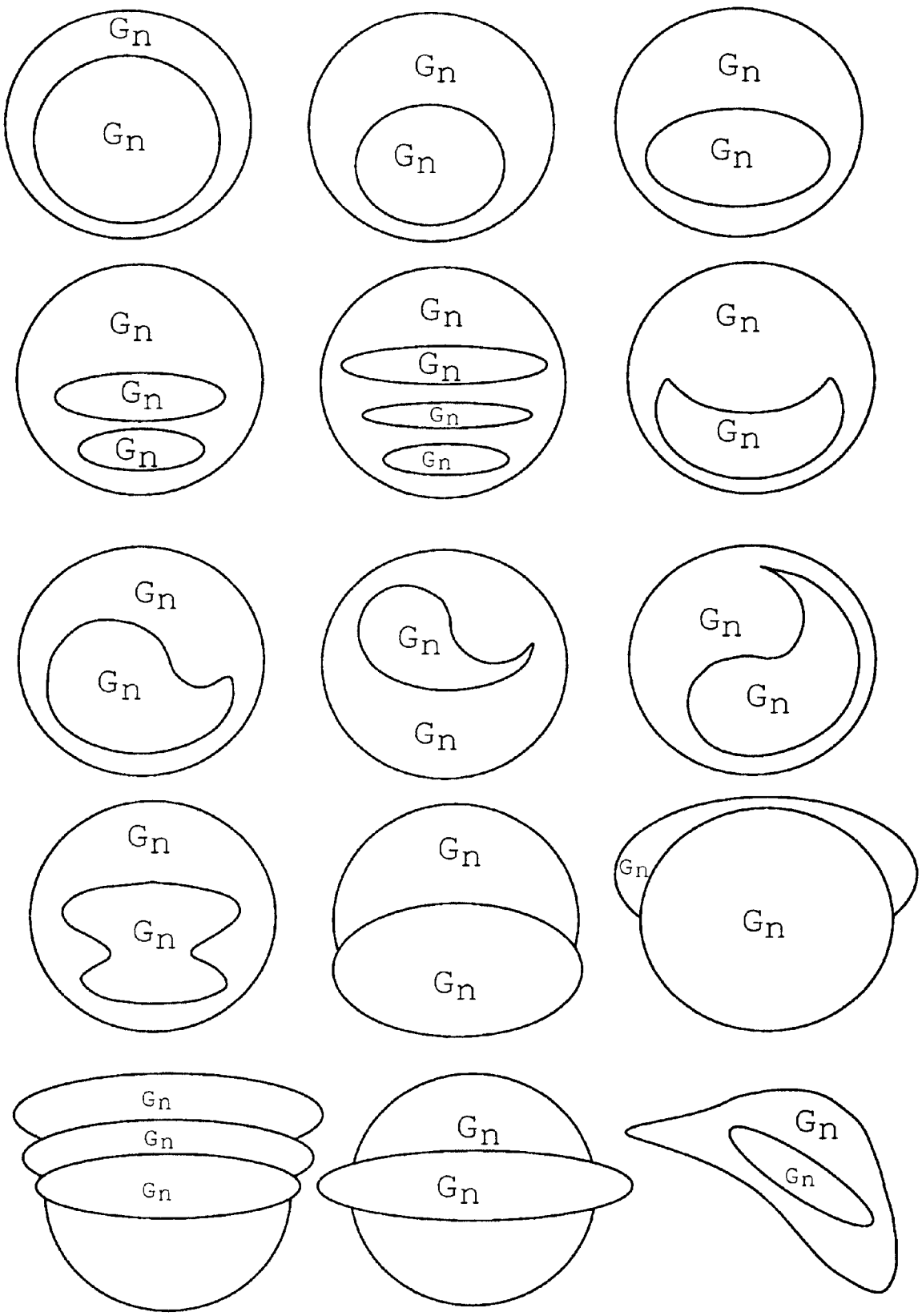
FIG. 5. Representative sectional views of various shaped airfoils with more than one gel regions.
Figure 6:
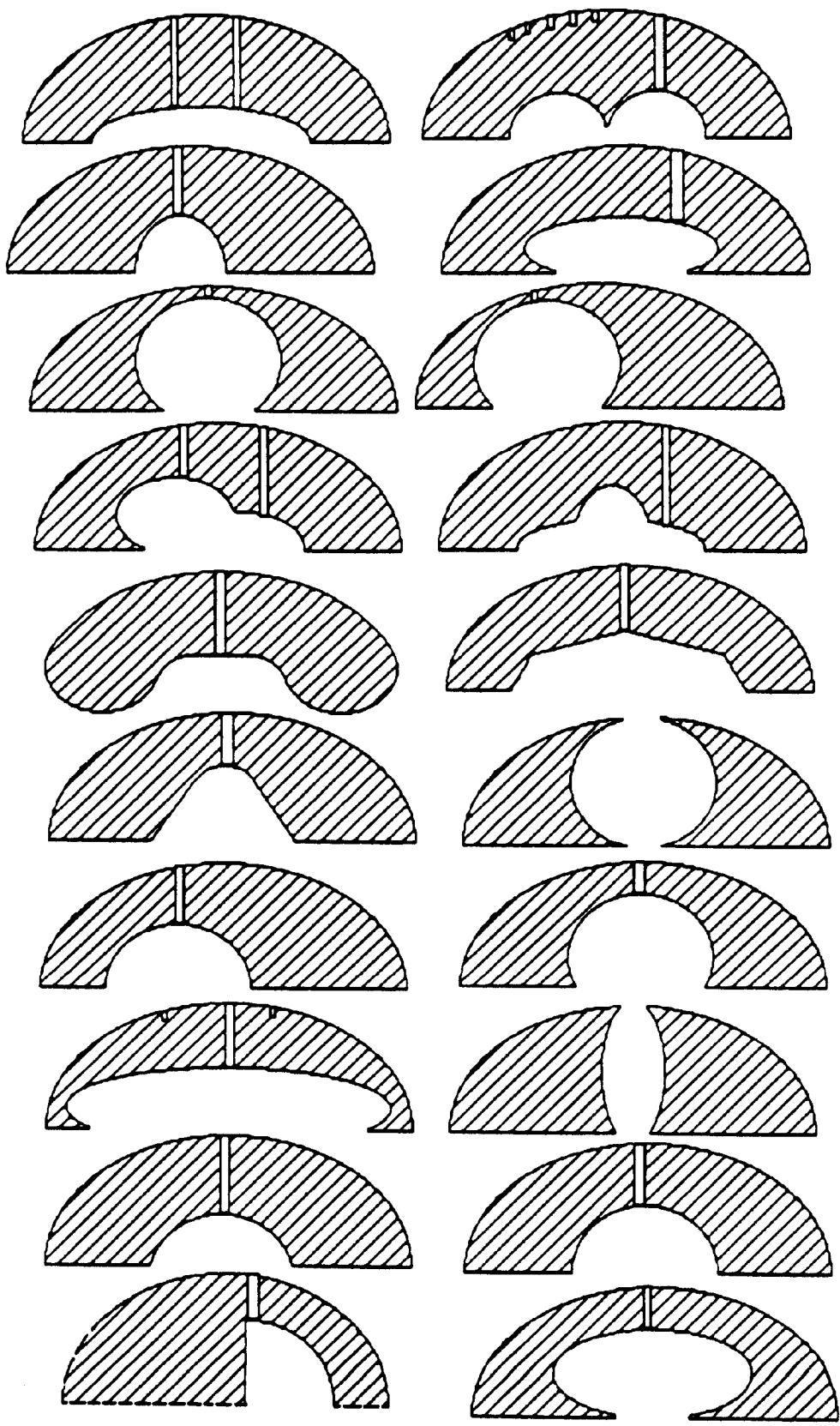
FIG. 6. More representative sectional views of shaped airfoils with holes, cavities, and slots.
Figure 7:
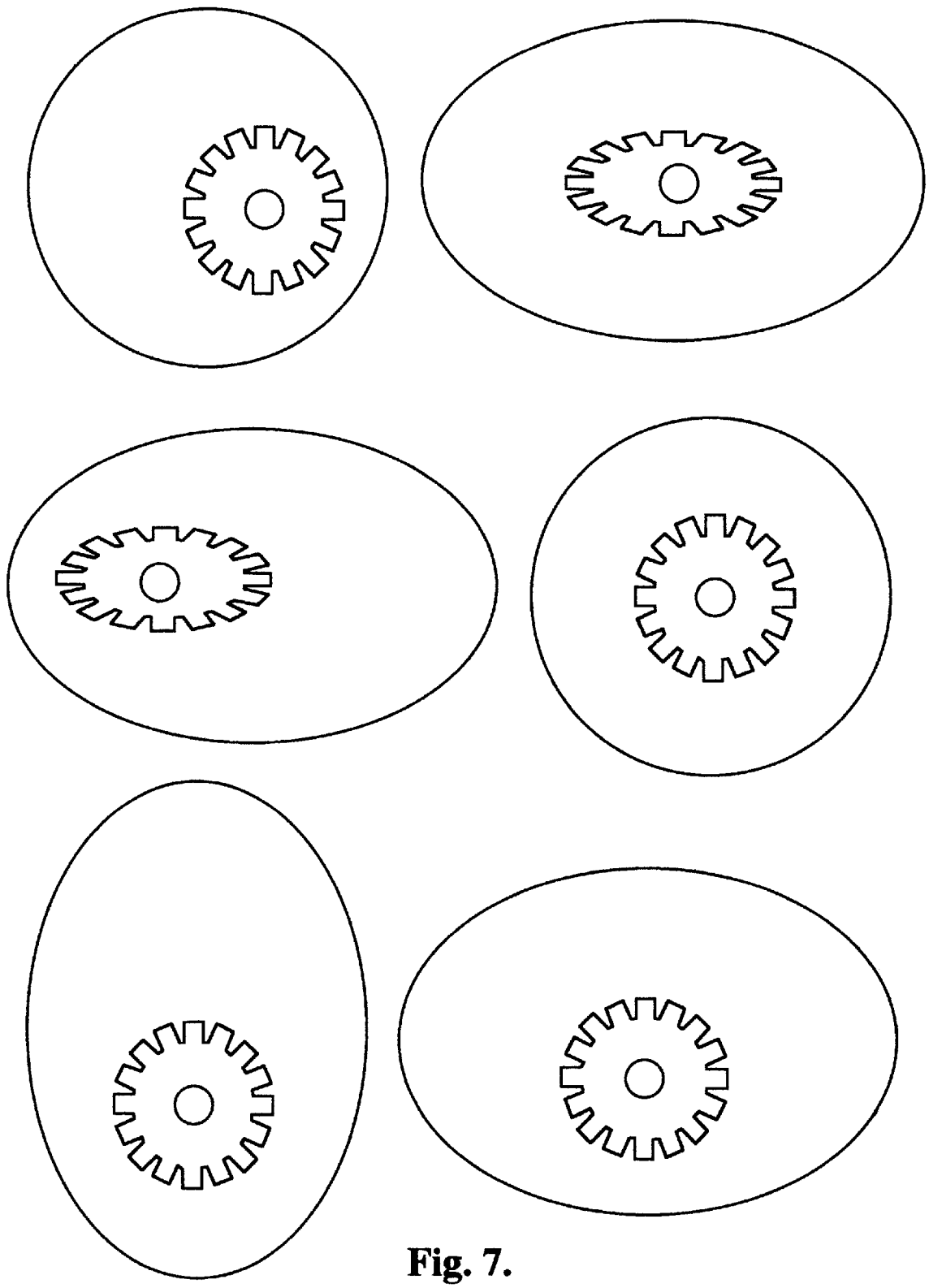
FIG. 7. Bottom view of airfoils showing a hole centered through a cavity.
Figure 8:
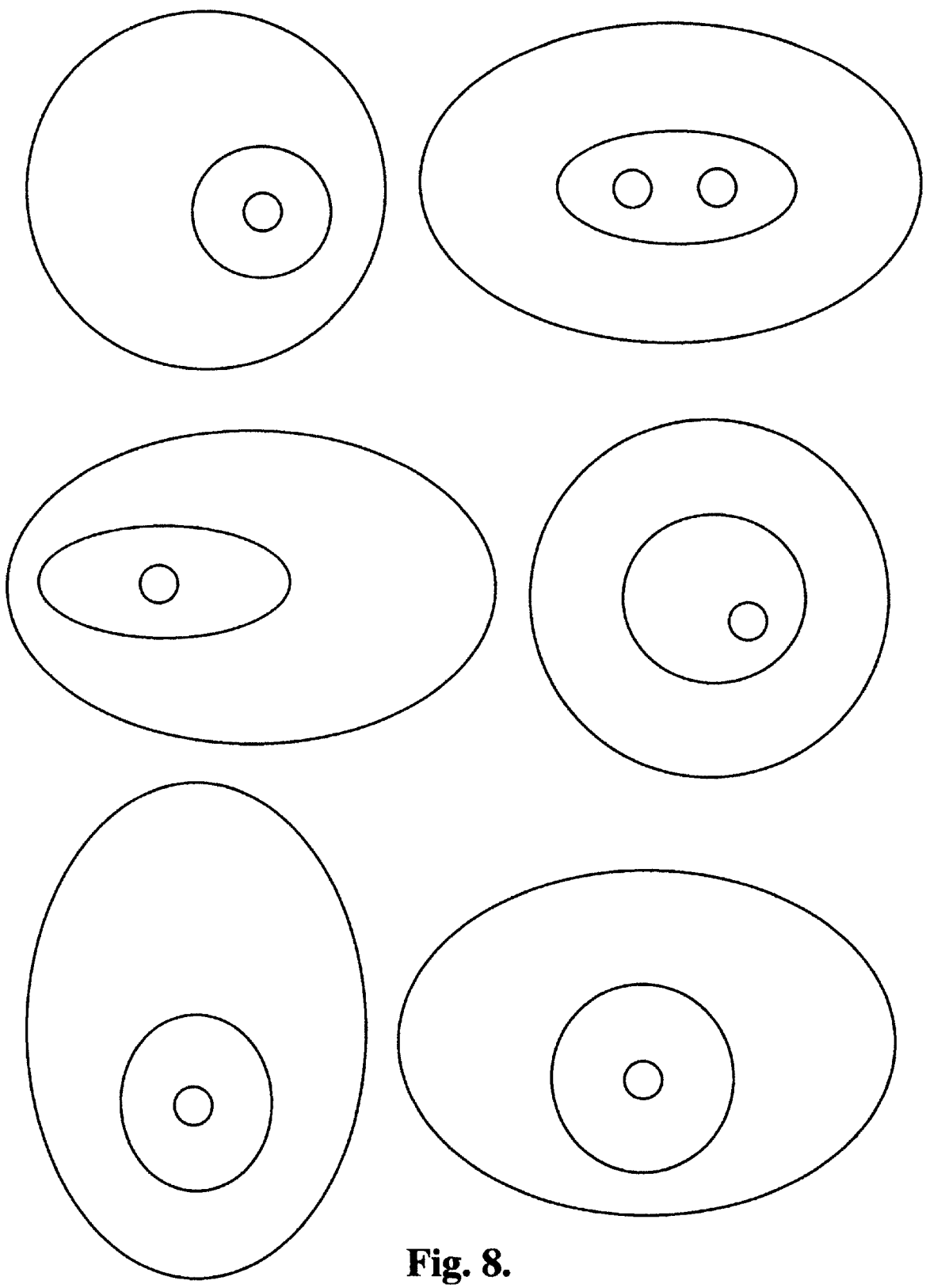
FIG. 8. Bottom view of airfoils showing a hole centered through a cavity.
Figure 9:
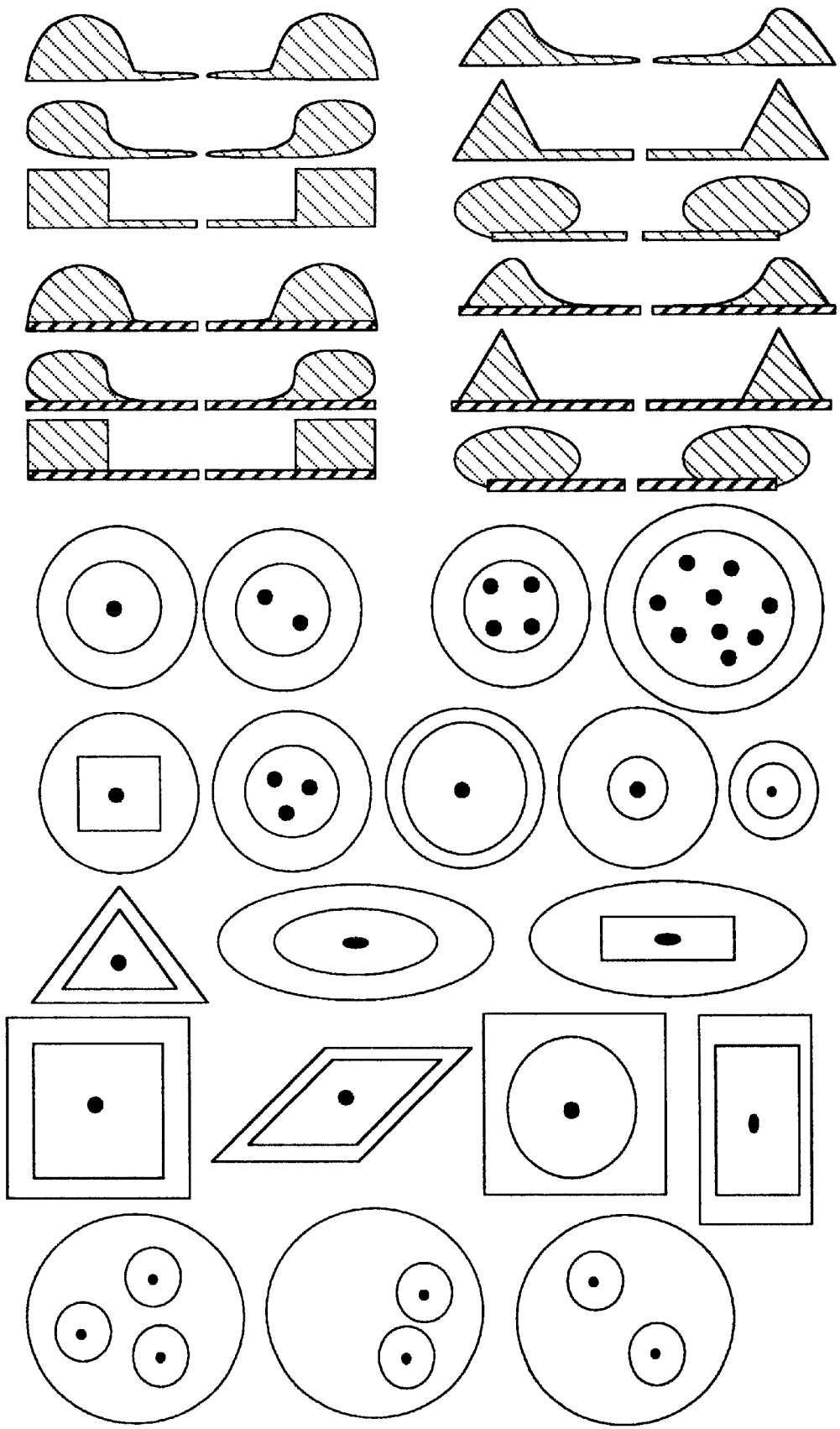
FIG. 9. Cross sectional view of membrane airfoils with hole and top view of membrane airfoils with one or more holes.
Figure 10:
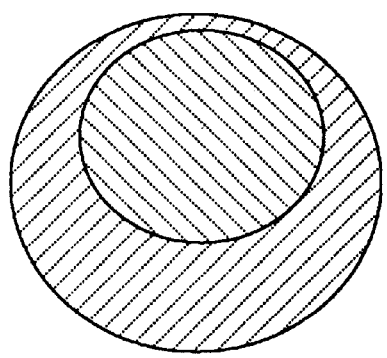
FIG. 10a. Representative cross sectional view of spherical shaped airfoil with two gel regions.
FIG. 10b. Cross sectional view of FIG. 10a airfoil resting on a support.
Figure 10:
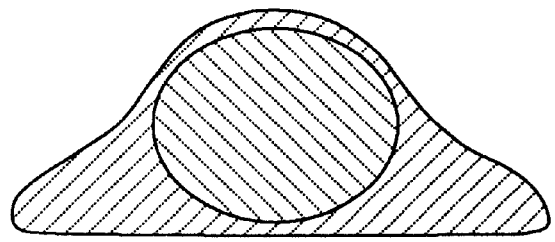
Figure 11:
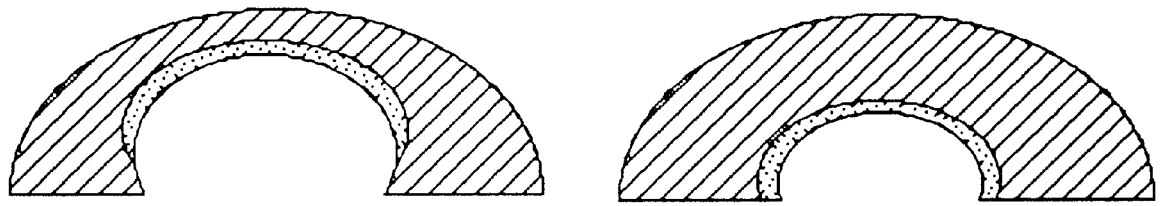
FIG. 11. Cross sectional views of airfoils with foam layers.
Figure 11:
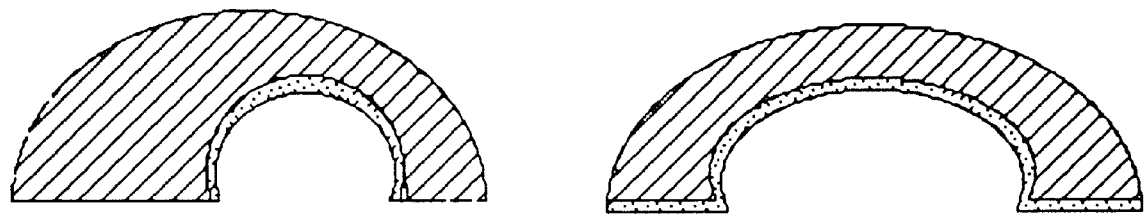

The crystal gel airfoils of the invention comprises a thickness envelope wrapped around a mean camber line as shown in FIG. 1. The 1989, 7th Edition of Van Nostrand's Scientific Encyclopedia defines camber as follows: "The carved line from the leading edge to the trailing edge of the airfoil is known as the camber. The curvature of the upper and lower surfaces, as well as a median line between them, is often referred to as camber or camber line."

The inner and outer parameter gel profiles for the crystal gel airfoil of the invention can be selected with mean camber lines. The mean camber line lies halfway between the upper and lower surfaces of the airfoil and intersects the chord line at the leading and trailing edges. The thickness envelope (bounded by an upper surface and a lower surface) of the airfoils of the invention can be of any suitable thickness provided the resulting airfoil is capable of sustained flight. Other geometrical variables of crystal gel airfoils of the invention are shown in FIG. 1; they include the cord line CL; the maximum camber $Z_c$ of the mean camber line and its distance $X_c$ behind the leading edge; the maximum thickness $t_{max}$ and its distance $x_t$ behind the leading edge; the radius of curvature of the surface at the leading edge, $r_o$, and the angle between the upper and lower surfaces at the trailing edge. In the design of the crystal gel airfoils of the invention, the geometrical variables should be selected so as to provide the instant airfoils with the ability for sustained flight in low as well as high wind conditions.

A suitable range for CL is less than about 3 cm to about 30 cm or more, typically 5 cm to 20 cm. The value (Xc–Xt)=Co can range from less than about 2 cm to greater than about 20 cm, typically 5 cm to 15 cm. The variable tmax can range from less than about 1 cm to greater than about 7 cm, typically 3 cm to 5 cm.

The inner and outer parameter aerodynamic gel profiles (i.e. cross-sectional geometry) of the airfoils of the invention can be varied as desired. A helpful way of designing and/or viewing the airfoils' profile from the side is to vertically cut the airfoils into adjacent slices. For example, the adjacent slices can be a series of different cross sections (i.e. cross sections of different geometrical variable values). A way to simulate the flight airfoil profile from the non-spinning static one is by deforming the airfoil profile approximate the same extend as sustained in flight. Another method is to spin the airfoil as discussed below.

The parameter gel profiles of the crystal gel airfoils can be sliced to show more than one cross sections. For example, viewing down on the upper surface, airfoils of the invention can have shapes such as a ring, circle, square, triangle, parallelogram, rhombus, trapezoid, quadrilateral, pentagon, hexagon, heptagon, octagon, nonagon, decagon, undecagon, dodecagon, polygon, sector, a circle, an ellipse, a parabola and the like.

The upper surface of the parameter gel profiles of the airfoils of the invention can be smooth, patterned, rough, and the like. In the case of an airfoil comprising one or more outer parameter gel profiles, the profile is formed with a connective thin gel membranes. During the time the airfoil is spinning, the gel membrane serves to control the degree of expansion and the rate of expansion of the profile from its original position as a function of rate of spin. Without such a thin gel membrane, the parameter profile can deform and expand out of control initially when the rate of spin is the highest, thereby substantially reducing lift due to a flatten or "far too stretched out" airfoil outer profile which prevents the airfoil to fly properly or not at all. The number and size of holes contained in the membrane of the airfoil connecting the parameter profile provides for adequate control of the expansion rate during spin. For example, two holes of the same size will allow the membrane to expand more than one hole of the same size, ten holes of the same size will allow the membrane to expand more than five holes of the same size; likewise, three holes of the same size will allow the profile to expand further than three holes of a smaller size. Therefore accurate control of the expansion rate of the outer profile of the airfoils of the invention can be established by selecting the placement of the holes, number of holes, and size of the holes contained in the membrane connecting the outer parameter profile. Moreover, the holes are in general serve as openings in the membrane; as such, the openings can be almost of any shape, such as square, triangle, parallelogram, rhombus, trapezoid, quadrilateral, pentagon, hexagon, heptagon, octagon, nonagon, decagon, undecagon, dodecagon, polygon, sector, a circle, an ellipse, and the like. The advantages of having one or more preselected number and sized holes is to improve handling, launching, and flight characteristics of the gel airfoils of the invention.

Although solid general prismatoid shapes such as spheroid shapes perform poorly in flight, most (such as a solid sphere) will not develop the required lift for sustained flight at any degree of spin. Lift can be imparted, however, to the solid general prismatoid shapes by modifying the solid shapes with an internal or external gel component having one or more substantially different gel rigidity regions, $G_n$, to so as to make the solid airfoil shapes non-symmetric, when n is a subscript of G, n denotes the same or a different gel rigidity of from about 2 gram to about 1,800 gram Bloom. See FIG. 6 for examples of various profiles. The additional requirements for forming general prismatoids with one or more internal and/or external regions are: (1) the resulting gel airfoils must have a sufficient volume of low gel rigidity region or regions for the bodies to exhibit a base diameter, D, (this is a measurable diameter advantageously of at least about 20% to 200% or more of the bodies' axes diameter and (2) a sufficient volume of high gel rigidity region or regions to allow a preselected volume of the bodies to support its own shape (i.e. moulded high gel rigidity shaped region) and exhibit a advantageously preselected amount of altitude, H, with a measurable height of about 20% or less to about 70% or more of the bodies' largest axes diameter (see FIGS. 9*a* and 9*b*). In order for the general prismatoids to have a base, the rigidity of the low gel rigidity region(s) should be at least about 50 gram Bloom or lower. A body formed in accordance with conditions (1) and (2) will exhibit a base when placed on a flat leveled surface of a preselected diameter. This base is defined as the surface area of contact of the body shape with the flat surface. For example, if a 6.5 cm diameter solid body shape is made from a uniformly high rigidity gel of say 80 gram Bloom or higher, the body will exhibit a base diameter of less than about 20% (less than about 1.3 cm) when place on a flat surface. Likewise, if a 6.5 cm diameter solid body shape is made from a uniformly low rigidity gel of say 20 gram Bloom or lower, the body will exhibit a base diameter greater than about 20% (greater than about 1.3 cm) when place on a flat surface. In both cases, the resulting low and high "uniform" gel solid body shapes will not have sufficient lift. If, however, one half of each of the low and high rigidity gel shapes are combined together, the resulting (non-uniform) solid body shape will exhibit a base diameter, D, greater than 20% of its axes diameter (due to the low rigidity half region ) and an altitude, H, of about 50% of its axes diameter or about 3.25 cm (due to the high rigidity half region). Such a nonuniform, unstremelined "blunt" shaped solid body will exhibit lift.

Various ways of making airfoils, such as forming a relatively low gel rigidity inner gel regions followed by a high gel rigidity outer (regions), are possible, as is the use of triple-layers (regions), etc. For example, the inner core of a general prismatoid shaped body can be made of urethane gel, the middle layer of silicone gel, and the outer layer of tear resistant gel with varying rigidity regions.

Less suitably, other thin materials can also take the place of the thin gel membranes of FIG. 11; such materials can include thin sheet members (e.g., laminated papers, films, laminated paper boards, sheet of various plastics and laminated plastics, fabrics, light metals foils and laminated metal foils, plastic or elastic foams and the like). Such thin sheet members are non-gels and do not extend as the gel membrane would under spin flight conditions. The gel profile can be formed unto the thin sheet member becoming an integral part of the thin sheet member in the form of a composite in accordance with copending U.S. application Ser. No. 288,690, filed Aug. 11, 1994.

Although the placement, shape and size of the gel profiles on the thin (non-gel) members (e.g. flat or contoured: paper, board, plastic, metal foil, foams, etc.) can be as shown in FIG. 11 in place of the membrane part of the airfoils, it has been discovered that the placement, shape and size of the gel profiles can be varied to a high degree. For example, the gel profile can be located on or near the outer parameter of the thin sheet members, it can also be located in a zig zag, or spiral pattern on the surface of the thin sheet members. Almost anywhere would do, provided the gel profiles are centered or balanced about the geometrical center of the thin sheet member useful as an airfoil. The size of the profile can also vary from 2 cm or greater to 3 mm or less. The shape and size of the gel profile selected in combination with a thin (non-gel) sheet member should provide adequate lift under spin flight conditions.

Over many thousands of launches of hundreds of different gel airfoil gel profiles under varying wind conditions, number and size of holes, and membrane thickness are observed to be of great advantage in their affects on flight characteristics of the gel airfoils of the invention. Holes of preselected sizes also provide airfoil stability during flight and prevent turn over. Membranes shows great advantage for use in connecting parts of the airfoil and control stretching of the connected parts during flight. It is observed that holes of preselected size will provide level and stable flight. It is observed that a selected thickness membrane in combination with one or more holes is of advantage to provide essential control of airfoil profile stretching and stable, level flight without turn over.

It is advantage for the hole diameter in the airfoil membrane to be about 0.2 cm to about 1.5 cm, more typically about 0.1 cm to about 1 cm, and especially about 0.1 cm to about 0.5 cm. Where it is desirable to have the smallest holes in the membrane, multiple holes can be distributed over the entire surface of the membrane.

The advantage size of the holes is about 0.2 cm to about 1.5 cm diameter, typically from about 0.2 cm to about 1.0 cm, more typically from about 0.2 cm to about 0.8 cm. The ratio of the airfoil base diameter (mean camber line length) to the hole diameter should be at least about 5 and greater. For example, if an airfoil's mean camber line is 7.5 cm, then any of the hole diameter should be no greater than about 1.5 cm.

The lower surface can be curved to any desired degree (centered or off-centered), or it can contain one or more cavities (centered or off-centered) of any desired shape.

The crystal gel airfoils of the invention can be launched by hand. Launching aids can also be used to grip the trailing edge of the airfoils such as a "U" shaped device to simulate the fingers and thumb. Normally, an airfoil of the invention is launched with a spin of the wrist. The spinning wrist action imparts rotation to the airfoil so as to elongate the airfoil as it leaves the hand. It is at the points of release by the hand that the gel airfoil experiences its highest stress and most subject to failure due to tearing of the gel body. The elongated airfoil will continue to spin and maintain its flight path while at the same time reach a maximum elongation due to centrifugal force and then retract back to its original shape as the spin reach a maximum and slows to a stop. Elongations of the airfoils (as measured from leading edge to trailing edge) under flight conditions can reach 50% or more. Elongations of 100%, 200%, 300%, 400%, 500%, 600%, 700% and higher are possible under flight conditions. Airfoils of the invention can be designed to withstand elongations higher than 1,000% which can occur at extreme high spin speeds.

Airfoils of the invention can fly at rotational speeds, Rs, of less than about 10 rpm to greater than about 1,500 rpm, typically 200 rpm to 1,000 rpm. Under such conditions, the profile deforms and elongates. The profile deform to a greater extend initially when the rate of spin is the greatest and recover gradually back to its original shape as the rate of spin decreases. Consequently, the profile deforms initially into a streamline shape at the start of flight (when drag can be highest due to high forward speed) and the profile becomes more and more blunt towards the end of the flight path providing more lift when drag is lowest because of lower forward speed of the airfoil. The instant airfoils can be launched at speeds, SI, less than about 5 mph to about 80 mph and higher, typically 15 mph to about 50 mph. Airfoils were tested in the laboratory and in the field using a few simple equipment. Airfoils were mounted on a variable spinning device. The rotational speeds were measured by using a GenRad 1546 digital stroboscope. Both natural and laboratory winds were measured using a Hall Airspeed Indicator. Laboratory winds (up to 55 mph) were generated using a Rotron Inc. Centrimax® model CXH33 Blower and wind tunnel assembly. Airfoil characteristics such as: angle of attack, geometrical profile, climb, drag, lift, Reynolds number, stall, rotational velocity, aspect ratio, stall, twist, pitch, sides angle, cord length, yaw angle, deformations, vibrations, air circulation and the like can be observed, measured and/or calculated under a variety of flight conditions.

Two Reynolds Numbers can be used to characterize the airfoils of the invention. These are: Re1 and Re2.

$$Re\mathbf{1}=\{[SI-Rs(CL/2)]Co\}/Vu,r$$

and $$Re\mathbf{2}=\{[SI+Rs(CL/2)]Co\}/Vu,r$$

where Vu,r=Viscosity/Density or approximate=0.15 cm2/second in air. Re1 and d Re2 can range from less than about 200 to about 100,000 or more. More suitably, Re1, and Re2 can range from less than about 5000 to about 50,000 and higher.

The instant crystal gel airfoils can fly under almost any wind condition, almost no wind (0.01 m.p.h.), low wind (0.5 m.p.h.), light wind (0.6 m.p.h.), moderate light wind (15 m.p.h.), moderate wind (25 m.p.h.), high wind (35 m.p.h.) and even under wind gust conditions greater than 40 m.p.h.

Block copolymers with polyethylene midblocks alone do not form suitable gels for use in making the airfoils of the invention. Crystalline midblock regions needs to be balanced with amorphous midblock regions in order to obtain soft, flexible and elastic gels with the desired crystalline properties that are not found in totally amorphous gels.

The polymers forming the gels of the invention comprises crystalline/glassy domain/amorphous structures which are described and illustrate in copending application Ser. No. 863,794. Although the structure can be spheroid, cylinders and plates are also within the scope of the present invention. Cylinder and plate structure are obtained with increasing glassy A end blocks. From about 15–30% by weight of A blocks, the block-copolymer structure is spheroid. From about 33 about 40% by weight of A blocks, the block copolymer structure becomes cylindrical; and above about 45% A blocks, the structure becomes less cylindrical and more plate like.

In order to obtain elastic crystal gels forming the airfoils of the invention, it is necessary that the selective synthesis of butadiene produce sufficient amounts of 1,4 poly (butadiene) that on hydrogenation can exhibit "crystallinity" in the midblocks. In order for the block copolymers forming the crystal gels of the invention to exhibit crystallinity, the crystalline midblock segments must contain long runs of $—CH_2—$ groups. There should be approximately at least 16 units of $—(CH_2)—$ in sequence for crystallinity. Only the $(—CH_2—)_4$ units can crystallize, and then only if there are at least 4 units of $(-CH_2-)_4$ in sequence; alternatively, the polyethylene units are denoted by $[-(CH_2-CH_2-CH_2-CH_2)-]_4$, $[(-CH_2-)_4]^4$ or $(-CH_2-)^{16}$. The amount of $(-CH_2-)^{16}$ units forming the (E) midblocks of the block copolymers comprising the crystal gels of the invention should be at least about 20% which amount is capable of exhibiting a melting endotherm in differential scanning calorimeter (DCS) curves.

Advantageously, the elastomer midblock segment should have a crystallinity of at least about 20% of $(-CH_2-)16$ units of the total mole % forming the midblocks of the block copolymer, more advantageously at least about 25%, still more advantageously at least about 30%, especially advantageously at least about 40% and especially more advantageously at least about 50% and higher. Broadly, the crystallinity of the midblocks should range from at least about 20% to about 60%, less broadly from at least about 18% to about 65%, and still less broadly from at least 22% to about 70%.

The melting endotherm in DSC curves of the crystalline block copolymers comprising at least 20% crystallinity are much higher than conventional amorphous block copolymers. The maximum in the endotherm curves of the crystalline block copolymers occurs at about 40° C., but can range from greater than about 25° C. to about 60° C. and higher. The crystalline block copolymers forming the crystal gels of the invention can exhibit melting endotherms (as shown by DSC) of about 25° C. to about 75° C. and higher. More specific melting endotherm values of the crystalline midblock block copolymers include: about 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 90° C., 100° C., 110° C., 120° C., and higher, whereas, the melting endotherm (DSC) for conventional amorphous midblock segment block copolymers are about 10° C. and lower.

The melting endotherm is seen on heating and a sharp crystallization exotherm is seen on cooling. Such midblock crystallization endothermic and exothermic characteristics are missing from DCS curves of amorphous gels. The crystallization exotherm and fusion endotherm of the crystalline block copolymer gels of the invention are determined by ASTM D 3417 method.

Generally, the method of obtaining long runs of crystalline $-(CH_2)-$ is by sequential block copolymer synthesis followed by hydrogenation. The attainment of crystal gels of the instant invention is solely due to the selective polymerization of the butadiene monomer (forming the midblocks) resulting in one or more predetermined amount of 1,4 poly(butadine) blocks followed by sequential polymerization of additional midblocks and hydrogenation to produce one or more crystalline midblocks of the final block copolymers.

The crystalline block copolymers are made by sequential block copolymer synthesis, the percentage of crystallinity or $(-CH_2-)^{16}$ units should be at least about $(0.67)^4$ or about 20% and actual crystallinity of about 12%. For example, a selectively synthesized $S-EB_n-S$ copolymer having a ratio of 33:67 of 1,2 and 1,4 poly(butadiene) on hydrogenation will result in a midblock with a crystallinity of $(0.67)^4$ or 20%. For sake of simplicity, when n is a subscript of -EB-, n denotes the percentage of $(-CH_2-)_4$ units, eg, n=33 or 20% crystallinity which is the percentage of $(0.67)^4$ or "$(-CH_2-)_{16}$" units. Thus, when n=28 or 72% of $(-CH_2-)_4$ units, the % crystallinity is $(0.72)^4$ or 26.87% crystallinity attributed to $(-CH_2-)_{16}$ units, denoted by $-EB_{28}-$. As a matter of convention, and for purposes of this specification involving hydrogenated polybutadiene: the notation -E- denotes at least about 85% of $(-CH_2-)_4$ units. The notation -B- denotes at least about 70% of $[-CH_2-CH(C_2H_5)-]$ units. The notation -EB- denotes between about 15 and 70% $[-CH_2-CH(C_2H_5)-]$ units. The notation $-EB_n-$ denotes n % $[-CH_2-CH(C_2H_5)-]$ units. For hydrogenated polyisoprene: The notation -EP- denotes about at least 90% $[-CH_2-CH(CH_3)-CH_2-CH_2-]$ units.

Generally, one or more (E) midblocks can be incorporated at various positions along the midblocks of the block copolymers. Using the sequential process for block copolymer synthesis, The (E) midblocks can be positioned as follows:

i) A-E-W-A ii) A-E-W-E-A ii) A-W-E-W-A iii) A-E-W-E-W-E-W-E-A iv) A-W-E-W-A-E-A-E-W-E-A v) and etc.

The lower flexibility of block copolymer crystal gels due to (E) midblocks can be balanced by the addition of sequentially (W) midblocks. For example, the sequentially synthesized block copolymer S-E-EB-S can maintain a high degree of flexibility due to the presence of amorphous -EB- block. The sequential block copolymer S-E-EB-B-S can maintain a high degree of flexibility due to the presence of amorphous -EB- and -B- midblocks. The sequential block copolymer S-E-EP-E-S can maintain a high degree of flexibility due to the presence of -EP- midblock. The sequential block copolymer S-E-B-S can maintain a high degree of flexibility due to the presence of the -B- midblock. For S-E-S, where the midblock is substantially crystalline and flexibility low, physical blending with amorphous block copolymers such as S-EB-S, S-B-S, S-EP-S, S-EB-EP-S, $(S-EP)_n$ and the like can produce more softer, less rigid, and more flexible crystal gel.

Because of the (E) midblocks, the crystal gels forming the airfoils of the invention exhibit different physical characteristics and improvements over substantially amorphous gels including damage tolerance, improved crack propagation resistance, improved tear resistance producing knotty tears as opposed to smooth tears, crystalline melting point of at least 28° C., improved resistance to fatigue, higher hysteresis, etc. Moreover, the crystal gels forming the airfoils when stretched exhibit additional yielding as shown by necking caused by stress induced crystallinity. Additionally, the crystallization rates of the crystalline midblocks can be controlled and slowed depending on thermal history producing time delay recovery upon deformation. Gels exhibiting time delay recovery following deformation is of great advantage and an improvement in the airfoil art.

The spinning gel airfoil when released is acted on by four forces. These are: force of gravity, centrifugal force, aerodynamic forces, and the elastic force. The elastic force is counter acted by the centrifugal force due to spin. Without the centrifugal force, an expanded gel airfoil will return to its original shape in approximately less than one tenth at a second. Therefore it is of great advantage to be able to expand, twist, stretch, depress, and in any way deform a airfoil shape or profile in any selective manner the thrower desires so that the deformed airfoil shape or profile essentially remains in the deformed state during substantially the entire time of flight. Gels having such time delay recovery properties are unique as airfoils. Such gels of the invention can achieve delay times of from about less than 2 seconds to about 20 seconds or more. Characteristic delay times that can be achieved are from about 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 120, seconds and longer. The shape and profiles of such airfoils are no longer dependent entirely on the centrifugal force. Consequentially, instead of the four forces, the force of stress induced crystallization or simply the time delay recovery force.

Regarding resistance to fatigue, fatigue (as used herein) is the decay of mechanical properties after repeated application of stress and strain. Fatigue tests give information about the ability of a material to resist the development of cracks or crazes resulting from a large number of deformation cycles. Fatigue test can be conducted by subjecting samples of amorphous and crystal gels to deformation cycles to failure (appearance of cracks, crazes, rips or tears in the gels).

Tensile strength can be determined by extending a selected gel sample to break as measured at 180° U bend around a 5.0 mm mandrel attached to a spring scale. Likewise, tear strength of a notched sample can be determined by propagating a tear as measured at 180° U bend around a 5.0 mm diameter mandrel attached to a spring scale.

Various block copolymers can be obtained which are amorphous, highly rubbery, and exhibiting minimum dynamic hysteresis:

Block Copolymer S-EB-S

The monomer butadiene can be polymerized in a ether/hydrocarbon solvent to give a 50/50 ratio of 1,2 poly (butadiene)/1,4 poly(butadiene) and on hydrogenation no long runs of —$CH_2$— groups and negligible crystallinity, ie, about $(0.5)^4$ or 0.06 or 6% and actual crystallinity of about 3%. Due to the constraints of $T_g$ and minimum hysteresis, conventional S-EB-S have ethylene-butylene ratios of about 60:40 with a crystallinity of about $(0.6)^4$ or 0.129 or 12% and actual crystallinity of about 7.7%.

Block Copolymer S-EP-S

The monomer isoprene when polymerized will produce 95% 1,4 poly(isoprene)/5% 3,4 poly(isoprene) and upon hydrogenation will form amorphous, rubbery poly(ethylene-propylene) midblock and no long runs of —$CH_2$— and no crystallinity.

Mixed Block Copolymer S-EB/EP-S

The polymerization of a 50/50 mixture of isoprene/butadiene monomers in suitable ether/hydrocarbon solvents to give equal amounts of 1,2 and 1,4 poly(butadiene) on hydrogenation will produce a maximum crystallinity of $(0.25)^4$ or 0.4%. The actual crystallinity would be approximately about 0.2%, which is negligible and results in a good rubbery midblock.

The polymerization of a 80/20 mixture of isoprene/butadiene monomers in suitable ether/hydrocarbon solvents to give equal amounts of 1,2 and 1,4 poly(butadiene) will upon hydrogenation produce a low crystallinity of $(0.10)^4$ or 0.01%. The actual crystallinity would be approximately about 0.006%, which is negligible and results in a good rubbery midblock.

The polymerization of a 20/80 mixture of isoprene/butadiene monomers in suitable ether/hydrocarbon solvents to give equal amounts of 1,2 and 1,4 poly(butadiene) will upon hydrogenation produce a low crystallinity of $(0.4)^4$ or 2.56%. The actual crystallinity would be approximately about 1.53%, which is negligible and results in a good rubbery midblock.

The polymerization of a 20/80 mixture of isoprene/butadiene monomers in suitable ether/hydrocarbon solvents to give a 40:60 ratio of 1,2 and 1,4 poly(butadiene) will upon hydrogenation produce a low crystallinity of $(0.48)^4$ or 5.3%. The actual crystallinity would be approximately about 3.2%, which is negligible and results in a good rubbery midblock.

The midblocks (Z) of one or more -E-, -B-, -EB-, or -EP- can comprise various combinations of midblocks between the selected end blocks (A); these include:

-E-EB-, -E-EP-, -B-EP-, -B-EB-, -E-EP-E-, -E-EB-B-, -B-EP-B-, -B-EB-B-, -E-B-EB-, -E-B-EP-, -EB-EP-, -E-EB-EP-, -E-EP-EB-, -B-EB-EP-, -B-EP-EB-, -E-EP-E-EP-, -E-EP-E-EB-, -B-EP-B-EP-, -B-EB-B-EB-, -B-EB-B-EP-, -E-EB-B-EP-, -E-EP-B-EB-, -E-EP-E-EP-E-, -B-EP-B-EP-B-, -E-EP-E-EB-, -E-EP-E-EP-EB-, -E-EP-E-EP-E-, -E-EP-EB-EP-EB-B- and the like.

The block copolymers of (A-Z-A) can be obtained by sequential synthesis methods followed by hydrogenation of the midblocks. As denoted above, abbreviations are interchangeably used, for example, (S-E-EP-S) denotes poly (styrene-ethylene-ethylene-co-propylene-styrene). Other linear block copolymers (denoted in abbreviations) include the following:

(S-E-S), (S-E-EB-S), (S-E-EP-S), (S-B-EP-S), (S-B-EB-S), (S-E-EP-E-S), (S-E-EB-B-S), (S-B-EP-B-S), (S-B-EB-B-S), (S-E-B-EB-S), (S-E-B-EP-S), (S-EB-EP-S), (S-E-EB-EP-S), (S-E-EP-EB-S), (S-B-EB-EP-S), (S-B-EP-EB-S), (S-E-EP-E-EP-S), (S-E-EP-E-EB-S), (S-EP-B-EP-S), (S-B-EB-B-EB-S), (S-B-EB-B-EP-S), (S-E-EB-B-EP-S), (S-E-EP-B-EB-S), (S-E-EP-E-EP-E-S), (S-B-EP-B-EP-B-S), (S-E-EP-E-EB-S), (S-E-EP-E-EP-EB-S), (S-E-EP-E-EP-E-S), (S-E-EP-EB-EP-E-EB-S), (S-E-EP-EB-EP-EB . . . -S) and the like.

The multiblock star-shaped (or radial) copolymers $(A–Z)_n X$ can be obtained by sequential synthesis methods including hydrogenation of selected block copolymers made by polymerizing half of the block copolymers such as SBS or SIS and couple the halves with a coupling agent such as an organic dihalide; or couple with an agent such as SnCl4, which results in star-shaped block copolymers (four branches). Coupling with divinyl benzene give block copolymers which are very highly branched. Radial block copolymers suitable for use in forming the crystal gels of the present invention include:

$(S-E)_n$, $(S-E-EB)_n$, $(S-E-EP)_n$, $(S-B-EP)_n$, $(S-B-EB)_n$, $(S-E-EP-E)_n$, $(S-E-EB-B)_n$, $(S-B-EP-B)_n$, $(S-B-EB-B)_n$, $(S-E-B-EB)_n$, $(S-E-B-EP)_n$, $(S-EB-EP)_n$, $(S-E-EB-EP)_n$, $(S-E-EP-EB)_n$, $(S-B-EB-EP)_n$, $(S-B-EP-EB)_n$, $(S-E-EP-E-EP)_n$, $(S-E-EP-E-EB)_n$, $(S-EP-B-EP)_n$, $(S-B-EB-B-EB)_n$, $(S-B-EB-B-EP)_n$, $(S-E-EB-B-EP)_n$, $(S-E-EP-B-EB)_n$, $(S-E-EP-E-EP-E)_n$, $(S-B-EP-B-EP-B)_n$, $(S-E-EP-E-EB)_n$, $(S-E-EP-E-EP-EB)_n$, $(S-E-EP-E-EP-E)_n$, $(S-E-EP-EB-EP-EB-B)_n$ and counter part multifunctional block copolymers: $(R)_n$-E-S, $(R)_n$-E-EB-S, $(R)_n$-E-EP-S, $(R)_n$-E-EP-E-S, $(R)_n$E-EB-B-S, $(R)_n$-E-B-EB-S, $(R)_n$-E-B-EP-S, $(R)_n$-E-EB-EP-S, $(R)_n$-E-EP-EB-S, $(R)_n$-E-EP-E-EP-S, $(R)_n$-E-EP-E-EB-S, $(R)_n$-E-EB-B-EP-S, $(R)_n$-E-EP-B-EB-S, $(R)_n$-E-EP-E-EP-E-S, $(R)_n$-E-EP-E-EB-S, $(R)_n$-E-EP-E-EP- EB-S, $(R)_n$-E-EP-E-EP-E-S, $(R)_n$-E-EP-EB-EP-EB-B-S, $(R)_n$-E-EP-EB-EP-EB . . . -S, and the like. In the above notation, "-E-" denotes substantially crystalline polyethylene midblock.

The selected amount of crystallinity in the midblock should be sufficient to achieve improvements in one or more physical properties including improved damage tolerance, improved crack propagation resistance, improved tear resistance, improved resistance to fatigue of the bulk gel and resistance to catastrophic fatigue failure of crystal gel composites, such as between the surfaces of the crystal gel and substrate or at the interfaces of the interlocking material (s) and crystal gel, which improvements are not found in amorphous gels at corresponding gel rigidities.

Selected (I) linear block and radial copolymers utilized in forming the crystal gels forming the airfoils of the invention are characterized as having an ethylene to butylene midblock ratio (E:B) of about 85:15 to about 65:35. Advantageously, the butylene concentration of the midblock is about 35% or less, more advantageously, about 30% or less, still more advantageously, about 25% or less, especially advantageously, about 20% or less. Advantageously, the ethylene to butylene midblock ratios can range from about 89:11, 88:12, 87:13, 86:14, 85:15, 84:16, 83:17, 82:18, 81:19, 80:20, 79:21, 78:22, 77:23, 76:24, 75:25, 74:26, 73:27, 72:28, 71:29, 70:30, 69:31, 68:32, 67:33, 66:34 to about 65:35.

The A to Z midblock ratio of the block copolymers suitable for forming crystal gels of the invention can range from about 20:80 to 40:60 and higher. More specifically, the values can be 15:85, 19:81, 20:80, 21:79. 22:78. 23:77, 24:76, 25:75, 26:74, 27:73, 28:72, 29:71, 30:70, 31:69, 32:68, 33:67, 34:66, 35:65, 36:64, 37:63, 38:62, 39:61, 40:60, 41:59, 42:58, 43:57, 44:65, 45:55, 46:54, 47:53, 48:52, 49:51, 50:50, 51:49 and 52:48.

The crystal gels forming the airfoils can optionally comprise selected major or minor amounts of one or more polymers or copolymers (II) provided the amounts and combinations are selected without substantially decreasing the desired properties. The polymers and copolymers can be linear, star-shaped (radial), branched, or multiarm; these including: (SBS) styrene-butadiene-styrene block copolymers, (SIS) styrene-isoprene-styrene block copolymers, low and medium viscosity (S-EB-S) styrene-ethylene-butylene-styrene block copolymers, (S-EP) styrene-ethylenepropylene block copolymers, (S-EP-S) styrene-ethylene/propylene-styrene block copolymers, (S-EP-S-EP) styrene-ethylene/propylene-styrene-ethylene/propylene) block copolymers, (S-E-EPS) styrene-ethylene-ethylene/propylene-styrene block copolymers, $(SB)_n$, styrene-butadiene and $(S-EB)_n$, $(S-EB-S)_n$, $(S-E-EP)_n$, $(SEP)_n$, $(SI)_n$ multi-arm, branched or star-shaped copolymers, polyethyleneoxide (EO), poly (dimethylphenylene oxide), teflon (TFE, PTFE, PEA, FEP, etc), optical clear amorphous copolymers based on 2,2-bistrifluoromethyl-4,5-difluoro-1,3-dioxole (PDD) and tetrafluoroethylene (TFE), maleated S-EB-S block copolymer, polycarbonate, ethylene vinyl alcohol copolymer, and the like. Still, other (II) polymers include homopolymers which can be utilized in minor amounts; these include: polystyrene, polydimethylsiloxane, polyolefins such as polybutylene, polyethylene, polyethylene copolymers, polypropylene,and the like. polyurethane elastomers based on saturated hydrocarbon diols (Handlin, D., Chin. S., and Masse. M., et al. "POLYURETHANE ELASTOMERS BASED ON NEW SATURATED HYDROCARBON DIOLS" published Society of plastics Industry, polyurethane Division, Las Vegas, Oct. 23, 1996) are also suitable for use in blending with the block copolymers (I) used in forming the crystal gels of the invention. Such saturated hydrocarbon diols include hydroxyl terminated oligomers of poly(ethylene-butylene) (EB), poly(ethylene-propylene) (EP),-E-EB-, -E-EP-, -B-EP-, -B-EB-, -E-EP-E-, -E-EB-B-, -B-EP-B-, -B-EB-B-, -E-B-EB-, -E-B-EP-, -EB-EP, -EB-EP-, -E-EP-EB-, -B-EB-EP-, -B-EP-EB-, -E-EP-E-EP-, -E-EP-E-EB-, -B-EP-B-EP-, B-EB-B-EB-, -B-EB-B-EP-, -E-EB-B-EP-, -E-EP-B-EB-, -E-EP-E-EP-E-, -B-EP-B-EP-B-, -EP-E-EB-, -E-EP-E-EP-EB-, -E-EP-E-EP-E-, -E-EP-EB-EP-EB-B- and the like. As an example, thermoplastic polyurethane made with isocyanates and chain extenders such as TMPD and BEPD from saturated hydrocarbon diol KLP L-2203 having a hard segment contents of 22% exhibits clean phase separation of the hard and soft segments with a glass transition of –50° C. KLP L-2203 based TPU's can be mixed with the crystalline block copolymers to form soft crystal gels within the gel rigidity ranges of the invention.

Suitable polyolefins include polyethylene and polyethylene copolymers such as Dow Chemical Company's Dowlex 3010, 2021D, 2038, 2042A, 2049, 2049A, 2071, 2077, 2244A, 2267R; Dow Affinity ethylene alpha-olefin resin PL-1840, SE-1400, SM-1300; more suitably: Dow Elite 51010, 5110, 5200, 5400, Primacor 141-XT, 1430, 1420, 1320, 3330, 3150, 2912, 3340, 3460; Dow Attane (ultra low density ethylene-octene-1 copolymers) 4803, 4801, 4602.

The conventional term "major" means about 51 weight percent and higher (e.g. 55%, 60%, 65%, 70%, 75%, 80% and the like) and the term "minor" means 49 weight percent and lower (e.g. 2%, 5%, 10%, 15%, 20%, 25% and the like).

Example of (II) polymers, copolymers, and blends include: (a) Kraton G 1651, G 1654X; (b) Kraton G 4600; (c) Kraton G 4609; other suitable high Viscosity polymer and oils include: (d) Tuftec H 1051; (e) Tuftec H 1041; (f) Tuftec H 1052; (g) Kuraray SEPS 4033; (h) Kuraray S-EB-S 8006; (i) Kuraray SEPS 2005; (j) Kuraray SEPS 2006, and (k) blends (polyblends) of (a)–(h) with other polymers and copolymers include: (1) S-EB-S/SBS; (2) S-EB-S/SIS; (3) S-EB-S/(SEP); (4) S-EB-S/$(SEB)_n$; (5) S-EB-S/$(SEB)_n$; (6) S-EB-S/$(SEP)_n$; (7) S-EB-S/$(SI)_n$; (8) S-EB-S/(SI) multi-arm; (9) S-EB-S/$(SEB)_n$; (10) $(SEB)_n$ star-shaped copolymer; (11) s made from blends of (a)–(k) with other homopolymers include: (12) S-EB-S/polystyrene; (13) S-EB-S/polybutylene; (14) S-EB-S/poly-ethylene; (14) S-EB-S/polypropylene; (16) SEP/S-EB-S, (17) SEP/SEPS, (18) SEP/SEPS/SEB, (19), SEPS/S-EB-S/SEP, (20), SEB/S-EB-S (21), EB-EP/S-EB-S (22), S-EB-S/EB (23), S-EB-S/EP (24), (25) $(SEB)_n$ s, (26) $(SEP)_n$, (27) Kuraray 2007 (SEPS), (28) Kuraray 2002, (SEPS), (29) Kuraray 4055 (S-E-EP-S) (30) Kuraray 4077 (S-E-EP-S) (31) Kuraray 4045 (S-E-EP-S) (32) (S-EB-EP)$_n$, (33) $(SEB)_n$, (34) EPDM, (35) EPR, (36) EVR, (37) copp, (38) EMA, (39) EER, (40) Dupont Teflon AF amorphous fluoropolymers, (41) Dow polydimethylsiloxane, (42) maleated S-EB-S (maleation level 2–30%), (43) $(EP)_n$ and the like.

Representative examples of commercial elastomers that can be combined with the block copolymers (I) described above include: Shell Kratons D1101, D1102, D1107, D1111, D1112, D1113X, D1114X, D1116, D1117, D1118X, D1122X, D1125X, D1133X, D1135H, D1184, D1188X, D1300X, D1320X, D4122, D4141, D4158, D4240, D1650, D1652, D1657, G1701X, G1702X, G1726X, G1750X, G1765X, FG1901X, FG1921X, D2103, D2109, D2122X, D3202, D3204, D3226, D5298, D5999X, D7340, G1650, G1651, G1652, G4609, G4600, G1654X, G2701, G2703, G2705, G1706, G2721X, G7155, G7430, G7450, G7523X, G7528X, G7680, G7705,G7702, G7720, G7722X, G7820, G7821X, G7827, G7890X, G7940, G1730M, FG1901X and FG1921X. Kuraray's SEP, SEPS, S-EB-S, S-EB-EP-S S-E-EP-S Nos. 1001, 1050, 2027, 2003, 2006, 2007, 2008, 2023, 2043, 2063, 2050, 2103, 2104, 2105, 4033, 4045, 4055, 4077, 8004, 8106, 8307, H-VS-3 (S-V-EP)N, and the like.

The amorphous S-EB-S and $(S-EB)_n$ (II) copolymers can have a broad range of styrene to ethylene-butylene ratios (S:EB) of about 20:80 or less to about 40:60 or higher. The S:EB weight ratios can range from lower than about 20:80 to above about 40:60 and higher.

The Brookfield Viscosity of a 5 weight percent solids solution in toluene at 30° C. of 2006, 4045, 4055, 4077 typically range about 20–35, about 25–150, about 60–150, about 200–400 respectively. Typical Brookfield Viscosities of a 10 weight percent solids solution in toluene at 30° C. of 1001, 1050, 2007, 2063, 2043, 4033, 2005, 2006, are about 70, 70, 17, 29, 32, 50, 1200, and 1220 respectively. Typical Brookfield Viscosity of a 25 weight percent solids solution in toluene at 25° C. of Kraton D1101, D1116, D1184, D1300X, G17011X, G1702X are about 4000, 9000, 20000, 6000, 50000 and 50000 cps respectively. Typical Brookfield Viscosity of a 10 weight percent solids solution in toluene at 25° C. of G1654X is about 370 cps. The Brookfield Viscosities of a 20 and 30 weight percent solids solution in toluene at 30° C. of H-VS-3 are about 133 cps and 350 cps respectively.

Suitable block copolymers (II) and their typical viscosities are further described. Shell Technical Bulletin SC:1393-92 gives solution Viscosity as measured With a Brookfield model RVT viscometer at 25° C. for Kraton G 1654X at 10% weight in toluene of approximately 400 cps and at 15% weight in toluene of approximately 5,600 cps. Shell publication SE:68-79 gives solution viscosity at 25° C. for Kraton G 1651 at 20 weight percent in toluene of approximately 2,000 cps. When measured at 5 weight percent solution in toluene at 30° C., the solution viscosity of Kraton G 1651 is about 40. Examples of high viscosity S-EB-S triblock copolymers includes Kuraray's S-EB-S 8006 which exhibits a solution viscosity at 5 weight percent at 30° C. of about 51 cps. Kuraray's 2006 SEPS polymer exhibits a viscosity at 20 weight percent solution in toluene at 30° C. of about 78,000 cps, at 5 weight percent of about 27 cps, at 10 weight percent of about 1220 cps, and at 20 weight percent 78,000 cps. Kuraray SEPS 2005 polymer exhibits a viscosity at 5 weight percent solution in toluene at 30° C. of about 28 cps, at 10 weight percent of about 1200 cps, and at 20 weight percent 76,000 cps. Other grades of S-EB-S, SEPS, $(SEB)_n$, $(SEP)_n$ polymers can also be utilized in the present invention provided such polymers exhibits the required high viscosity. Such S-EB-S polymers include (high viscosity) Kraton G 1855X which has a Specific Gravity of 0.92, Brookfield Viscosity of a 25 weight percent solids solution in toluene at 25° C. of about 40,000 cps or about 8,000 to about 20,000 cps at a 20 weight percent solids solution in toluene at 25° C.

The styrene to ethylene and butylene (S:EB) weight ratios for the Shell designated polymers can have a low range of 20:80 or less. Although the typical ratio values for Kraton G 1651, 4600, and 4609 are approximately about 33:67 and for Kraton G 1855X approximately about 27:73, Kraton G 1654X (a lower molecular weight version of Kraton G 1651 with somewhat lower physical properties such as lower solution and melt viscosity) is approximately about 31:69, these ratios can vary broadly from the typical product specification values. In the case of Kuraray's S-EB-S polymer 8006 the S:EB weight ratio is about 35:65. In the case of Kuraray's 2005 (SEPS), and 2006 (SEPS), the S:EP weight ratios are 20:80 and 35:65 respectively. The styrene to ethylene-ethylene/propylene (S:E-EP) ratios of Kuraray's SEPTON 4045, 4055, and 4077 are typically about 37.6, 30, 30 respectively. More typically the (S:E-EP) and (S:EP) ratios can vary broadly much like S:EB ratios of S-EB-S and $(SEB)_n$ from less than 19:81 to higher than 51:49 (as recited above) are possible. It should be noted that multiblock copolymers including SEPTON 4045, 4055, 4077 and the like are described in my cited copending parent applications and are the subject matter of related inventions.

The block copolymers (II) such as Kraton G 1654X having ratios of 31:69 or higher can be used and do exhibit about the same physical properties in many respects to Kraton G 1651 while Kraton G 1654X with ratios below 31:69 may also be use, but they are less advantageous due to their decrease in the desirable properties of the final gel.

Plasticizers (III) particularly advantageous for use in practicing the present invention are will known in the art, they include rubber processing oils such as paraffinic and naphthenic petroleum oils, highly refined aromatic-free paraffinic and naphthenic food and technical grade white petroleum mineral oils, and synthetic liquid oligomers of polybutene, polypropene, polyterpene, etc. The synthetic series process oils are high viscosity oligomers which are permanently fluid liquid nonolefins, isoparaffins or paraffins of moderate to high molecular weight.

The amount of plasticizing oil (III) sufficient to achieve gel rigidities of from less than about 2 gram Bloom to about 1,800 gram Bloom range from less than about 250 to about 3,000 parts by weight of a plasticizing oil.

Examples of representative commercially available plasticizing oils include Amoco® polybutenes, hydrogenated polybutenes, polybutenes with epoxide functionality at one end of the polybutene polymer, liquid poly(ethylene/butylene), liquid hetero-telechelic polymers of poly(ethylene/butylene/styrene) with epoxidized polyisoprene and poly(ethylene/butylene) with epoxidized polyisoprene: Example of such polybutenes include: L-14 (320 Mn), L-50 (420 Mn), L-100 (460 Mn), H-15 (560 Mn), H-25 (610 Mn), H-35 (660 Mn), H-50 (750 Mn), H-100 (920 Mn), H-300 (1290 Mn), L-14E (27–37 cst @ 100° F. Viscosity), H-300E (635–690 cst @ 210° F. Viscosity), Actipol E6 (365 Mn), E16 (973 Mn), E23 (1433 Mn), Kraton L-2203 and Kraton L-1203, EKP-206, EKP-207, HPUM-2203 and the like. Example of various commercially oils include: ARCO Prime (55, 70, 90, 200, 350, 400 and the like), Duraprime and Tufflo oils (6006, 6016, 6016M, 6026, 6036, 6056, 6206, etc) , other white mineral oils include: Bayol, Bernol, American, Blandol, Drakeol, Eruol, Gloria, Kaydol, Litetek, Lyondell (Duraprime 55, 70, 90, 200, 350, 400, etc), Marcol, Parol, Peneteck, Primol, Protol, Sontex, Witco brand white oils including RR-654-P and the like. Generally, plasticizing oils with average molecular weights less than about 200 and greater than about 700 may also be used (e.g., H-300 (1290 Mn)).

Comparisons of oil extended S-EB-S triblock copolymers have been described in Shell Chemical Company Technical Bulletin SC:1102-89 (April 1989) "KRATON® THERMOPLASTIC RUBBERS IN OIL GELS" which is incorporated herein by reference.

The crystal gels forming the airfoils can be made non-adhearing, non-sticking, (non-tacky), by incorporating an advantage amount of stearic acid (octadecanoic acid), metal stearates (e.g., calcium stearate, magnesium stearate, zinc stearate, etc.), polyethylene glycol distearate, polypropylene glycol ester or fatty acid, and polytetramethylene oxide glycol disterate, waxes, stearic acid and waxes, metal stearate and waxes, metal stearate and stearic acid. The use of stearic acid alone do not reduce tack. The amount of stearic acid is also important. As an example, ratio of 200 grams stearic acid to 2,000 grant of S-EB-S (a ratio of 0.1) will result in spotted tack reduction on the surface of the gel. A ratio of 250 to 2,000 will result in spotted crystallized stearic acid regions on the surface of the gel or spotted tack reduction. A ratio of 300 to 2,000 will result in complete tack reduction with large stearic acid crystallized regions on the surface of the gel. When microcrystalline waxes are incorporated together with stearic acid, the crystallization of stearic acid completely disappears from the surface of the gel. For example excellent result is achieved with 200 grams of stearic acid, 150 grams of microcrystalline wax and 2,000 grams of S-EB-S. The same excellent result is achieved when S-EB-S is adjusted to 3,000 grams, 4,000 grams, etc. The same result is achieved with (I) copolymers as well as in combination with polymers (II) such as SEPS, S-EB-EP-S, (S-EB-EP)$_n$, (SEB)$_n$, (SEP)$_n$ polymers.

The crystal gels forming the airfoils can also contain useful amounts of conventionally employed additives such as stabilizers, antioxidants, antiblocking agents, colorants, fragrances, flame retardants, flavors, other polymers in minor amounts and the like to an extend not affecting or substantially decreasing the desired properties. Additives useful in the crystal gel of the present invention include: tetrakis[methylene 3,-(3'5'-di-tertbutyl-4"-hydroxyphenyl) propionatel methane, octadecyl 3-(3",5"-di-tert-butyl-4"-hydroxyphenyl)propionate, distearylpentaerythritol-diproprionate, thiodiethylene bis-(3,5-tert-butyl-4-hydroxy) hydrocinnamate, (1,3,5-trimethyl-2,4,6-tris[3,5-di-tert-butyl-4-hydroxybenzyl]benzene), 4,4"-methylenebis(2,6-di-tert-butylphenol), steraric acid, oleic acid, stearamide, behenamide, oleamide, erucamide, N,N"-ethylenebisstearamide, N,N"-ethylenebisoleamide, stearyl erucamide, erucyl erucamide, oleyl palmitamide, stearyl stearamide, erucyl stearamide, calcium sterate, other metal sterates, waxes (e.g., polyethylene, polypropylene, microcrystalline, carnauba, paraffin, montan, candelilla, beeswax, ozokerite, ceresine, and the like), teflon (TFE, PTFE, PER, FEP, etc), polysiloxane, etc. The crystal gel can also contain metallic pigments (aluminum and brass flakes), TiO2, mica, fluorescent dyes and pigments, phosphorescent pigments, aluminatrihydrate, antimony oxide, iron oxides ($Fe_3O_4$, —$Fe_2O_3$, etc.), iron cobalt oxides, chromium dioxide, iron, barium ferrite, strontium ferrite and other magnetic particle materials, molybdenum, silicones, silicone fluids, lake pigments, aluminates, ceramic pigments, ironblues, ultramarines, phthalocynines, azo pigments, carbon blacks, silicon dioxide, silica, clay, feldspar, glass microspheres, barium ferrite, wollastonite and the like. The report of the committee on Magnetic Materials, publication NMAB-426, National Academy press (1985) is incorporated herein by reference.

The crystal gels forming the airfoils can also be made into composites. The crystal gels can be casted unto various substrates, such as open cell materials, metals, ceramics, glasses, and plastics, elastomers, fluropolymers, expanded fluropolymers, Teflon (TEE, PTFE, PEA, FEP, etc), expanded Teflon, spongy expanded nylon, etc.; the molten crystal gel is deformed as it is being cooled. Useful open-cell plastics include: polyamides, polyimides, polyesters, polyisocyanurates, polyisocyanates, polyurethanes, poly (vinyl alcohol), etc. Suitable open-celled Plastic (sponges) are described in "Expanded plastics and Related products", Chemical Technology Review No. 221, Noyes Data Corp., 1983, and "Applied Polymer Science", Organic Coatings and Plastic Chemistry, 1975. These publications are incorporated herein by reference.

The crystal gels denoted as "G" can be formed with another gel of a different rigidity to form gel composites or physically interlocked with a selected material denoted as "M" to form composites as denoted for simplicity by their combinations $G_nG_n$, $G_nG_nG_n$, $G_nM_n$, $G_nM_nG_n$, $M_nG_nM_n$, $M_nG_nG_n$, $G_nG_nM_n$, $M_nM_nM_nG_n$, $M_nM_nM_nG_nM_n$, $M_nG_nG_nM_n$, $G_nM_nG_nG_n$, $G_nM_nM_nG_n$, $G_nM_nM_nG_n$, $G_nG_nM_nM_n$, $G_nG_nM_nG_nM_n$, $G_nM_nG_nG_n$, $G_nG_nM_n$, $G_nM_nG_nM_nM_n$, MnGnMnGnMnGn, $G_nG_nM_nM_nG_n$, $G_nG_nM_nG_nM_nG_n$, and the like or any of their permutations of one or more $G_n$ with $M_n$ and the like, wherein when n is a subscript of M, n is the same or different selected from the group consisting of foam, plastic, fabric, synthetic fibers or or films and the like; wherein when n is a subscript of G, n denotes the same or a different gel rigidity of from about 2 gram to about 1,800 gram Bloom. The crystal gels of the composites are formed from copolymers (I), polymers (II), and plasticizers (III) described above.

Sandwiches of crystal gel-material (i.e., crystal gel-material-crystal gel or material-crystal gel-material, etc.) are useful as dental floss, shock absorbers, acoustical isolators, vibration dampers, vibration isolators, and wrappers. For example the vibration isolators can be use under research microscopes, office equipment, tables, and the like to remove background vibrations. The tear resistance nature of the instant crystal gels are superior in performance to amorphous block copolymer gels which are much less resistance to crack propagation caused by long term continue dynamic loadings.

The crystal gels forming the airfoils are prepared by blending together the components including other additatives as desired at about 23° C. to about 100° C. forming a paste like mixture and further heating said mixture uniformly to about 150° C. to about 200° C. until a homogeneous molten blend is obtained. Lower and higher temperatures can also be utilized depending on the viscosity of the oils and amounts of multiblock copolymers (I) and polymer (II) used. These components blend easily in the melt and a heated vessel equipped with a stirrer is all that is required. Small batches can be easily blended in a test tube using a glass stirring rod for mixing. While conventional large vessels with pressure and/or vacuum means can be utilized in forming large batches of the instant crystal gels in amounts of about 40 lbs or less to 10,000 lbs or more. For example, in a large vessel, inert gases can be employed for removing the composition from a closed vessel at the end of mixing and a partial vacuum can be applied to remove any entrapped bubbles. Stirring rates utilized for large batches can range from about less than 10 rpm to about 40 rpm or higher.

The crystal gel articles can be formed by blending, injection molding, extruding, spinning, casting, dipping and other conventional methods. For example, Shapes having various cross-section call be extruded. The crystal gel can also be formed directly into articles or remelted in any suitable hot melt applicator and extruded into shaped articles and films or spun into threads, strips, bands, yarns, or other shapes. With respect to various shapes and yarn, its size are conventionally measured in denier (grams/9000 meter), tex (grams/1000 meter), and gage (1/2.54 cm). Gage, tex, denier can be converted as follows: tex=denier/9=specific gravity (2135/gage), for rectangular cross section, tex=specific gravity (5806×103)(th)(w)/9, where th is the thickness and w the width of the strip, both in centimeters. General descriptions of (1) block copolymers, (2) elastomeric fibers and conventional (3) gels are found in volume 2, starting at pp. 324–415, volume 6, pp 733–755, and volume 7, pp. 515 of *ENCYCLOPEDIA OF POLYMER SCIENCE AND ENGINEERING,* 1987 which volumes are incorporated herein by reference.

The crystal gels forming the airfoils are excellent for cast molding and the molded products have high tear resistance characteristics which cannot be anticipated form the properties of the raw components. Other conventional methods of forming the composition can be utilized.

Not only do the crystal gels forming the airfoils have all the desirable combination of physical and mechanical properties substantially similar to high viscosity amorphous S-EB-S gels such as high elongation at break of at least 1,600%, ultimate tensile strength of about $8 \times 10^5$ dyne/cm$^2$ and higher, low elongation set at break of substantially not greater than about 2%, substantially about 100% snap back when extended to 1,200% elongation, and a gel rigidity of substantially from about 2 gram to about 1,800 grain Bloom and higher, the crystal gels of the present invention exhibit improved tear resistance and resistance to fatigue not obtainable from amorphous S-EB-S or S-EP-S gels at corresponding gel rigidities.

The crystal gels forming the airfoils of the present invention exhibit one or more of the following properties. These are: (1) tensile strength of about $8 \times 10^5$ dyne/cm$^2$ to about $10^7$ dyne/cm$^2$ and greater; (2) elongation of less than about 1,600% to about 3,000% and higher; (3) elasticity modules of about $10^4$ dyne/cm$^2$ to about $10^6$ dyne/cm$^2$ and greater; (4) shear modules of about $10^4$ dyne/cm$^2$ to about $10^6$ dyne/cm$^2$ and greater as measured with a 1, 2, and 3 kilogram load at 23° C.; (5) gel rigidity of about less than about 2 grain Bloom to about 1,800 gram Bloom and higher as measured by the gram weight required to depress a gel a distance of 4 mm with a piston having a cross-sectional area of 1 square cm at 23° C.; (6) tear propagation resistance greater than the tear resistance of amorphous S-EB-S gels at corresponding gel rigidities; (7) resistance to fatigue greater than the fatigue resistance of amorphous S-EB-S gels at corresponding gel rigidities; (8) and substantially 100% snap back recovery when extended at a crosshead separation speed of 25 cm/minute to 1,200% at 23° C. properties (1), (2), (3), aid (6) above are measured at a crosshead separation speed of 25 cm/minute at 23° C.

The crystal gel articles molded from the instant crystal gels have additional important advantages in that the end-use performance properties are advantageously greater than amorphous S-EB-S gels in that they are more resistant to cracking, tearing, crazing or rupture in flexural, tension, compression, or other deforming conditions of use. Like amorphous gels, the molded articles made from the instant composition possess the intrinsic properties of elastic memory enabling the articles to recover and retain its original molded shape after many extreme deformation cycles.

Not only is the crystal gels of the invention advantageous for use in making gel airfoils, the novel crystal gels because of their improved properties find other piratical uses.

Because of their improved tear resistance and improved resistance to fatigue, the crystal gels of the present invention achieve greater performance than amorphous gels in low frequency vibration applications, such as viscoelastic layers in constrained-layer damping of mechanical structures and goods, as viscoelastic layers used in laminates for isolation of acoustical and mechanical noise, as anti-vibration elastic support for transporting shock sensitive loads, as vibration isolators for an optical table, as viscoelastic layers used in wrappings, enclosures and linings to control sound, as compositions for use in shock and dielectric encapsulation of optical, electrical, and electronic components.

Because of their improved tear resistance and improved resistance to fatigue, the crystal gels are more useful as molded shape articles for use in medical and sport health care, such use include therapeutic hand exercising grips, dental floss, crutch cushions, cervical pillows, bed wedge pillows, leg rest, neck cushion, mattress, bed pads, elbow padding, dermal pads, wheelchair cushions, helmet liner, cold and hot packs, exercise weight belts, traction pads and belts, cushions for splints, slings, and braces (for the hand, wrist, finger, forearm, knee, leg, clavicle, shoulder, foot, ankle, neck, back, rib, etc.), and also soles for orthopedic shoes. Other uses include various shaped articles as toys, optical uses (e.g., cladding for cushioning optical fibers from bending stresses) and various optical devices, as lint removers, dental floss, as tips for swabs, as fishing bate, as a high vacuum seal (against atmosphere pressure) which contains a useful amount of a mineral oil-based magnetic fluid particles, etc. Moreover, the casted, extruded, or spun threads, strips, yarns, tapes can be weaved into cloths, fine or coarse fabrics.

The crystal gels can be formed in any shape; the original shape can be deformed into another shape (to contact a regular or irregular surface) by pressure and upon removal of the applied pressure, the composition in the deformed shape will recover back to its original shape.

As an example of the versatility of use of the instant crystal gels, a hand exerciser can be made in any shape so long as it is suitable for use as a hand exerciser: a sphere shape, a cube shape, a rectangular shape, etc. Likewise, a wheelchair cushion can be made from the composition in any shape, so long as it meets the needs of the user of the cushion. For example, a cushion can be made by forming the composition into a selected shape matching the contours of the specific body part or body region. The composition can be formed into any desired shaped, size and thickness suitable as a cushion; the shaped composition can be additionally surrounded with film, fabric, foam, or any other desired material or combinations thereof. Moreover, the composition can be casted onto such materials, provided such materials substantially maintain their integrity (shape, appearance, texture, etc.) during the casting process. The same applies for brace cushions, liners, linings and protective coverings for the hand, wrist, finger, forearm, knee, leg, etc.

Because of their improved tear resistance and resistance to fatigue, the crystal gels exhibit versatility as balloons for medical uses, such as balloon for valvuloplasty of the mitral valve, gastrointestinal balloon dilator, esophageal balloon dilator, dilating balloon catheter use in coronary angiogram and the like. Since the crystal gels are more tear resistant, they are especially useful for making condoms, toy balloons, and surgical and examination gloves. As toy balloons, the crystal gels are safer because it will not rupture or explode when punctured as would latex balloons which often times cause injures or death to children by choking from pieces of latex rubber. The crystal gels are advantageously useful for making gloves, thin gloves for surgery and examination and thicker gloves for vibration damping which prevents damage to blood capillaries in the fingers and hand caused by handling strong shock and vibrating equipment.

Other uses include self sealing enclosures for splicing electrical and telephone cables and wires. For example, the crystal gels can be pre-formed into a small diameter tubing within an outer elastic tubing, both the internal crystal gel tubing and external elastic tubing can be axially expanded and fixed in place by a removable continuous retainer. Upon insertion of a spliced pair or bundle of cables or wires, the retainer can be removed, as the retainer is removed, the crystal gel and elastic tubing impinges onto the inserted cables or wires splices, thereby sealing the electrical splices against weather, water, dirt, corrosives and shielding the splice from external abuse. The enclosure is completed without the use of heat or flame as is conventionally performed.

Because of their improved resistance to tearing, the crystal gels do not tear as readily as amorphous gels when used as dental floss. The dental floss can be almost any shape so long as it is suitable for dental flossing. A thick shaped piece of the composition can be stretched into a trial shape and used for flossing. A thinner shaped piece would require less stretching, etc. for purposes of dental flossing, while flossing between two closely adjacent teeth, especially between two adjacent teeth with substantial contact points and more especially between two adjacent teeth with substantial amalgam alloy metal contact points showing no gap between the teeth, it is critical that the crystal gel resist tearing, shearing, and crazing while being stretched to a high degree in such situations. For example, dental crystal gel floss can take the form of a disk where the segments of the circumference of the disk is stretched for flossing between the teeth. Other shaped articles suitable for flossing include threads, strips, yarns, tapes, etc., mentioned above.

In all cases, the tear strength of crystal gels are higher than that of amorphous gels. For example, the crystal gels made from high Viscosity S-E-EB-S and S-E-EP-S copolymers are resistant to tearing when sheared than high viscosity amorphous S-EB-S and S-EP-S copolymer gels. This can be demonstrated by forming a very soft gel samples, for example 100 parts copolymer to 800 parts plasticizing oil. The soft gel is made in a 16 mm×150 mm, test tube, the gel cylinder is cut or notched at one point about its cross-section and gripped lengthwise tightly in the left hand about this cross-section point and a length of exposed gel is gripped lengthwise around the adjacent cross-section point tightly by the right hand as close to the left hand as possible without stretching. With the two hands gripping the gel sample's cross-section about the notched point, the hands are moved in opposite directions to tear apart the gel sample at the cross-section point. The shearing action by the gripping hands is done at the fastest speed possible as call be performed by human hands. Using this demonstration, the crystal gels will not easily break or tear completely apart, whereas, amorphous S-EB-S and S-EP-S gels break or tears apart easily. Likewise the various crystal gels of the invention described herein are tested and found to be more tear resistant than amorphous gels. For airfoils, the improved resistance to tearing is essential for acceptable performance during play.

While preferred components and formulation ranges have been disclosed herein. persons of skill in the art can extend these ranges using appropriate material according to the principles discussed herein. All such variations and deviations which rely on the teachings through which the present invention has advanced the art are considered to be within the spirit and scope of the present invention.

What I claim is:

1. An aerodynamic toy comprising a camber defined by a profile in the shape of an airfoil made from an ultra-elastic, tear resistant, crystal gel, said crystal gel comprising (I) one or more copolymers and at least one copolymer having a midblock of one or more substantially crystalline poly(ethylene) midblock segment, in combination with or without (II) a selected amount of one or more polymer or copolymer and (III) a selected amounts of one or more plasticizing oil sufficient to achieve gel rigidities of from less than about 2 gram Bloom to about 1,800 gram Bloom.

2. An aerodynamic toy comprising an ultra-elastic, tear resistant, crystal gel in the shape of an airfoil, said airfoil having an upper surface and an lower surface defining a camber, said crystal gel comprising (I) one or more copolymers and at least one copolymer having a midblock of one or more substantially crystalline poly(ethylene) midblock segment, said copolymers having the formula poly(styrene-ethylene-ethylene-butylene-styrene), poly(styrene-ethylene-ethylene-propylene-styrene), poly(styrene-ethylene-ethylene-propylene-ethylene-styrene), poly(styrene-ethylene-ethylene-butylene)$_n$, poly(styrene-ethylene-ethylene-propylene)$_n$, poly(styrene-ethylene-ethylene-propylene-ethylene)$_n$, wherein subscript n is two or more; said copolymers being in combination with or without (II) a selected amount of one or more polymer or copolymer, and (III) a selected amounts of one or more plasticizing oil sufficient to achieve a gel rigidity of from about 2 to about 1,800 gram Bloom, wherein said crystal gel is capable of exhibiting greater tear propagation resistance than a gel having a corresponding rigidity made from poly(styrene-ethylene-butylene-styrene) or poly(styrene-ethylene-propylene-styrene) block copolymers having substantially non-crystalline poly(ethylene) midblocks.

3. An aerodynamic toy comprising an ultra-elastic tear resistant, crystal gel in the shape of an airfoil defining a camber, said airfoil capable of exhibiting a time delay recovery from deformation of about at least one minute, said crystal gel comprising (I) one or more copolymers and at least one copolymer having a midblock of one or more substantially crystalline poly(ethylene) midblock segment, said copolymers having the formula poly(styrene-ethylene-ethylene-butylene-styrene), poly(styrene-ethylene-ethylene-propylene-styrene), poly(styrene-ethylene-ethylene-propylene-ethylene-styrene), poly styrene-ethylene-ethylene-butylene)$_n$, poly(styrene-ethylene-ethylene-propylene)$_n$, poly(styrene-ethylene-ethylene-propylene-ethylene)$_n$, wherein subscript n is two or more; said copolymers being in combination with or without (II) a selected amount of one or more polymer or copolymer, and (III) a selected amounts of one or more plasticizing oil sufficient to achieve a gel rigidity of from about 2 to about 1,800 gram Bloom, wherein said crystal gel is capable of exhibiting greater tear propagation resistance than a gel having a corresponding rigidity made from poly(styrene-ethylene-butylene-styrene) or poly(styrene-ethylene-propylene-styrene) block copolymers having substantially non-crystalline poly(ethylene) midblocks.

4. An aerodynamic toy comprising an ultra-elastic, tear resistant, crystal gel in the shape of an airfoil; said airfoil having an upper surface and a lower surface defining a camber; and said crystal gel capable of a time delay recovery from recovery of at least two minutes, said crystal gel comprising (I) one or more copolymers and at least one copolymer having a midblock of one or more substantially crystalline poly(ethylene) midblock segment, said copolymers having the formula poly(styrene-ethylene-ethylene-propylene-styrene), poly(styrene-ethylene-ethylene-propylene)$_n$, wherein subscript n is two or more; said copolymers being in combination with or without (II) a selected amount of one or more polymer or copolymer, and (III) a selected amounts of one or more plasticizing oil sufficient to achieve a gel rigidity of from about 2 to about 1,800 gram Bloom, wherein said crystal gel is capable of exhibiting greater tear propagation resistance than a gel having a corresponding rigidity made from poly(styrene-ethylene-butylene-styrene) or poly(styrene-ethylene-propylene-styrene) block copolymers having substantially non-crystalline poly(ethylene) midblocks.

5. An aerodynamic toy comprising an ultra-elastic, tear resistant, crystal gel in the shape of an airfoil, said airfoil having an upper surface and a lower surface defining a camber, said airfoil capable of exhibiting a time delay recovery from deformation of at least five seconds, said crystal gel comprising Ia one or more copolymers and at least one copolymer having a midblock of one or more substantially crystalline poly(ethylene) midblock segment, said copolymers having the formula poly(styrene-ethylene-ethylene-propylene-styrene), poly(styrene-ethylene-ethylene-propylene)$_n$, poly(styrene-ethylene-ethylene-butylene-styrene), or poly(styrene-ethylene-ethylene-butylene)$_n$, wherein subscript n is two or more; said copolymers being in combination with or without (II) a selected amount of one or more polymer or copolymer, and (III) a selected amounts of one or more plasticizing oil sufficient to achieve a gel rigidity of from about 2 to about 1,800 gram Bloom, wherein said crystal gel is capable of exhibiting greater tear propagation resistance than a gel having a corresponding rigidity made from poly(styrene-ethylene-butylene-styrene) or poly(styrene-ethylene-propylene-styrene) block copolymers having substantially non-crystalline poly(ethylene) midblocks.

6. An aerodynamic toy comprising a camber defined by a profile in the shape of an airfoil made from a low rigidity, tear resistant, crystal gel comprising (I) one or more copolymers and at least one copolymer having a midblock of one or more substantially crystalline poly(ethylene) midblock segment, said copolymers having the formula poly(styrene-ethylene-ethylene-propylene-styrene), poly(styrene-ethylene-ethylene-propylene)$_n$, poly(styrene-ethylene-ethylene-butylene-styrene), or poly(styrene-ethylene-ethylene-butylene)$_n$, wherein subscript n is two or more; said copolymers being in combination with or without (II) a selected amount of one or more polymer or copolymer, and (III) a selected amounts of one or more plasticizing oil sufficient to achieve a gel rigidity of from about 20 to about 1,800 gram Bloom, wherein said crystal gel is capable of exhibiting greater tear propagation resistance than a gel having a corresponding rigidity made from poly(styrene-ethylene-butylene-styrene) or poly(styrene-ethylene-propylene-styrene) block copolymers having substantially non-crystalline poly(ethylene) midblocks; and wherein said crystal gel comprising one or more copolymers having sufficient crystallinity as to exhibit a melting endotherm of about 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 90° C., 100° C., 110° C., or 120° C., as determined by DSC curve.

7. An aerodynamic toy comprising an ultra-elastic, tear resistant, crystal gel in the shape of an airfoil having an upper surface and an lower surface defining a camber, said crystal gel comprising (I) one or more of a hydrogenated poly(styrene-isoprene/butadiene-styrene) block copolymers (s) with 2-methyl-1,3-butadiene and 1,3-butadiene having a midblock of one or more substantially crystalline poly (ethylene) midblock segment, said copolymers having the formula poly(styrene-ethylene-ethylene-propylene-styrene), wherein said copolymers being in combination with or without (II) a selected amount of one or more polymer or copolymer, and (III) a selected amounts of one or more plasticizing oil sufficient to achieve a gel rigidity of from about 20 to about 1,800 gram Bloom, wherein said crystal gel is capable of exhibiting greater tear propagation resistance than a gel having a corresponding rigidity made from poly(styrene-ethylene-butylene-styrene) or poly(styrene-ethylene-propylene-styrene) block copolymers having substantially non-crystalline poly(ethylene) midblocks.

8. An airfoil according to claim 1, made from a composite of a gel, denoted by G, which is physically interlocked with a selected material M forming said gel composite of the combination $G_nG_n$, $G_nG_nG_n$, $G_nM_n$, $G_nM_nG_n$, $M_nG_nM_n$, $M_nG_nG_n$, $M_nM_nM_nG_n$, $M_nM_nM_nG_nM_n$, $M_nG_nG_nM_n$, $G_nM_nG_nG_n$, $G_nM_nM_nG_n$, $G_nG_nM_nM_n$, $G_nG_nM_nG_nM_n$, $G_nM_nG_nM_nM_n$, $M_nG_nM_nG_nM_nG_n$, $G_nG_nM_nM_nG_n$, $G_nG_nM_nG_nM_nG_n$, or a permutation of one or more of said $G_n$ with $M_n$, wherein when n is a subscript of M, n is the same or different selected from group consisting of foam, plastic, fabric, metal, synthetic resin, or synthetic fibers; and wherein when n is a subscript of G, n denotes the same or a different gel rigidity; said gel characterized by a gel rigidity of from about 2 gram to about 1,800 gram Bloom.

* * * * *